United States Patent

Burbank et al.

[11] Patent Number: 5,759,193
[45] Date of Patent: Jun. 2, 1998

[54] SINGLE NEEDLE SKIN STRETCHING DEVICE

[75] Inventors: John E. Burbank, Ridgefield, Conn.;
Charles L. Putnam, Bellemeade, N.J.;
Bernard Hirshowitz, Haifa, Israel

[73] Assignee: MedChem Products, Inc., Princeton, N.J.

[21] Appl. No.: 664,623

[22] Filed: Jun. 18, 1996

Related U.S. Application Data

[63] Continuation of Ser. No. 230,931, Apr. 21, 1994, abandoned.
[51] Int. Cl.$^6$ ................................. A61B 17/08
[52] U.S. Cl. ................ 606/213; 606/215; 606/216; 606/217; 606/151
[58] Field of Search ............... 606/212, 213, 606/215–218, 221, 150, 151, 149, 201, 219, 226, 227

[56] References Cited

U.S. PATENT DOCUMENTS

| | | |
|---|---|---|
| 268,632 | 12/1882 | Danforth . |
| 583,455 | 6/1897 | Bush . |
| 2,450,194 | 9/1948 | Glaser . |
| 2,669,747 | 2/1954 | Detaranto . |
| 3,971,384 | 7/1976 | Hasson . |
| 4,506,669 | 3/1985 | Blake, III . |
| 4,512,346 | 4/1985 | Lemole . |
| 4,535,772 | 8/1985 | Sheehan . |
| 4,747,394 | 5/1988 | Watanabe . |
| 4,834,112 | 5/1989 | Machek et al. ............ 128/20 |
| 4,896,680 | 1/1990 | Hirshowitz . |
| 5,009,663 | 4/1991 | Broome . |
| 5,047,047 | 9/1991 | Yoon . |

FOREIGN PATENT DOCUMENTS

| | | |
|---|---|---|
| 0 018 698 | 11/1980 | European Pat. Off. . |
| 0 269 935 | 6/1988 | European Pat. Off. . |
| 0 279 534 | 8/1988 | European Pat. Off. . |
| 418970 | 12/1910 | France . |
| 2272632 | 12/1975 | France . |
| 32 27 984 | 7/1982 | Germany . |
| 2001597 | 10/1993 | Russian Federation . |
| 848001 | 7/1981 | U.S.S.R. . |
| 1106489 | 8/1984 | U.S.S.R. . |
| 1412751 | 9/1986 | U.S.S.R. . |
| 1560132 | 4/1988 | U.S.S.R. . |
| 1560133 | 7/1988 | U.S.S.R. . |
| 1556666 | 4/1990 | U.S.S.R. . |

OTHER PUBLICATIONS

Cohen and Cosmetto, "Suture Tension Adjustment Reel", J. Dermatol. Surg. Oncol., 1992; 18:112–123.

Primary Examiner—Michael Buiz
Assistant Examiner—Tina T.D. Pham
Attorney, Agent, or Firm—Fulbright & Jaworski LLP

[57] ABSTRACT

One or more devices for stretching skin to close a wide skin defect may be used with two long interdermal needles which are inserted underneath the skin along margins of the wound. The skin stretching device may include a pair of needle shafts each having a hook or needle at a distal end for engaging one of the interdermal needles, and a contracting mechanism provided for drawing the opposing needle hooks toward one another, thereby approximating the opposing margins of the wound.

The skin stretching device may also include a control knob for limiting the amount of force applied by the device, and a tension indicator for indicating the amount of force applied by the device. Each elongated shafts may also exhibit a retaining member about which a swivel platform rotates, and to which two or more needles are attached. The skin stretching device may further include elongated shafts which, at their distal ends, angle away from the body of the shafts, each exhibiting a single needle. Finally, the skin stretching device may include curved shafts which exhibit one or more needles at their distal ends.

43 Claims, 21 Drawing Sheets

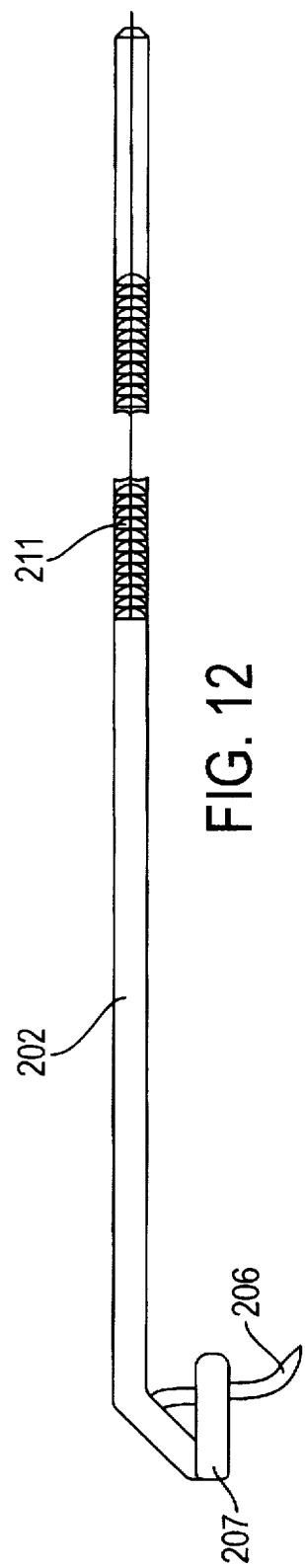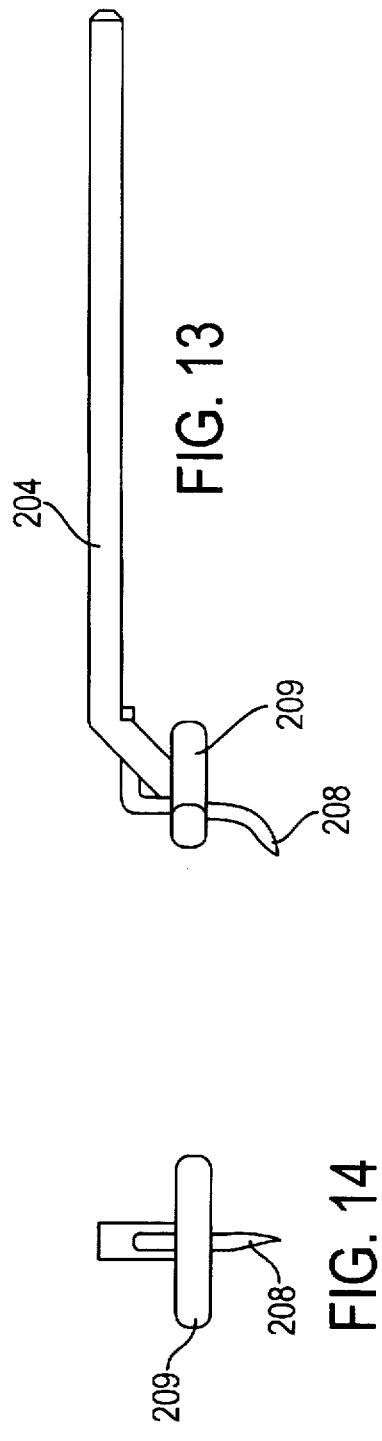

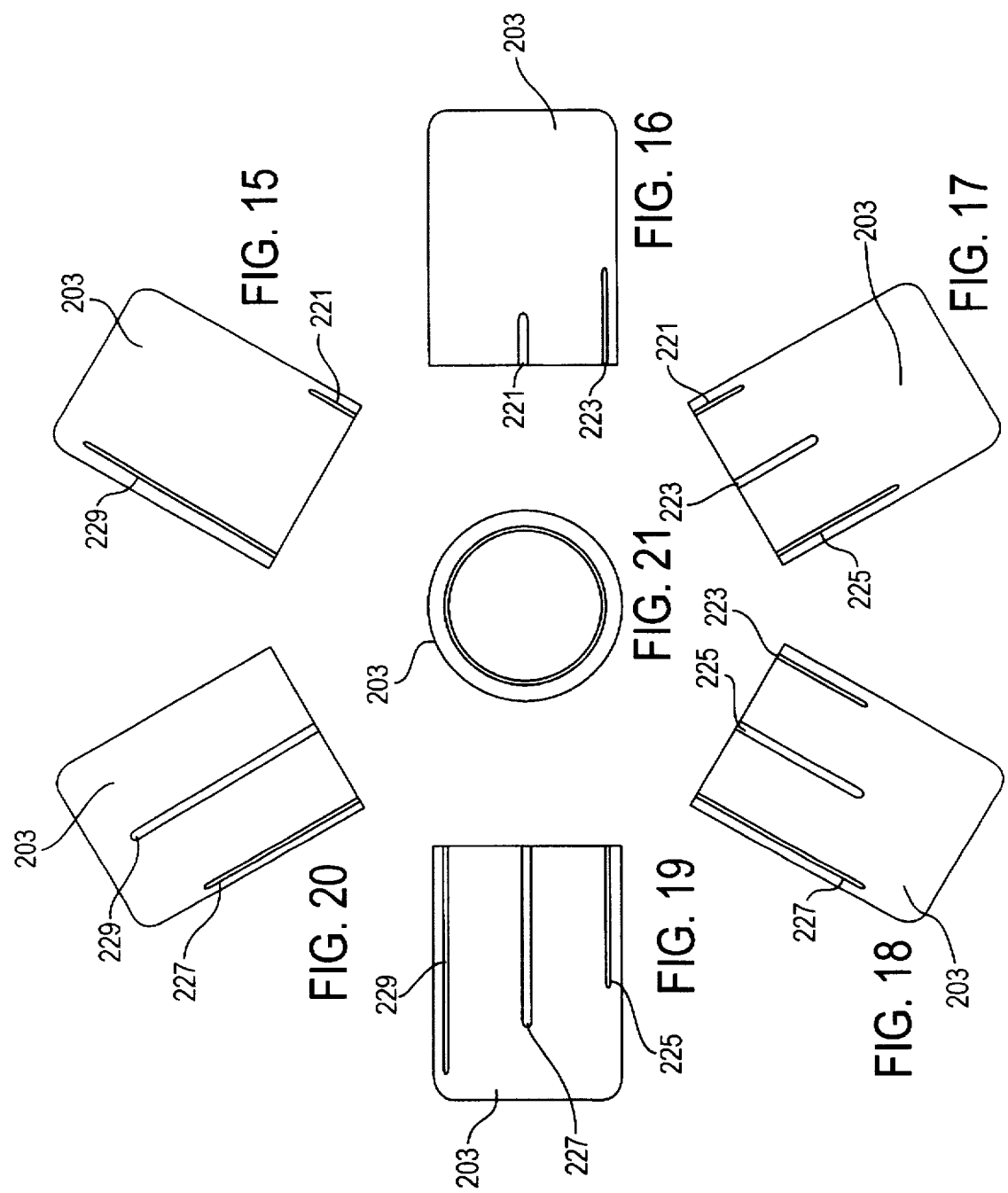

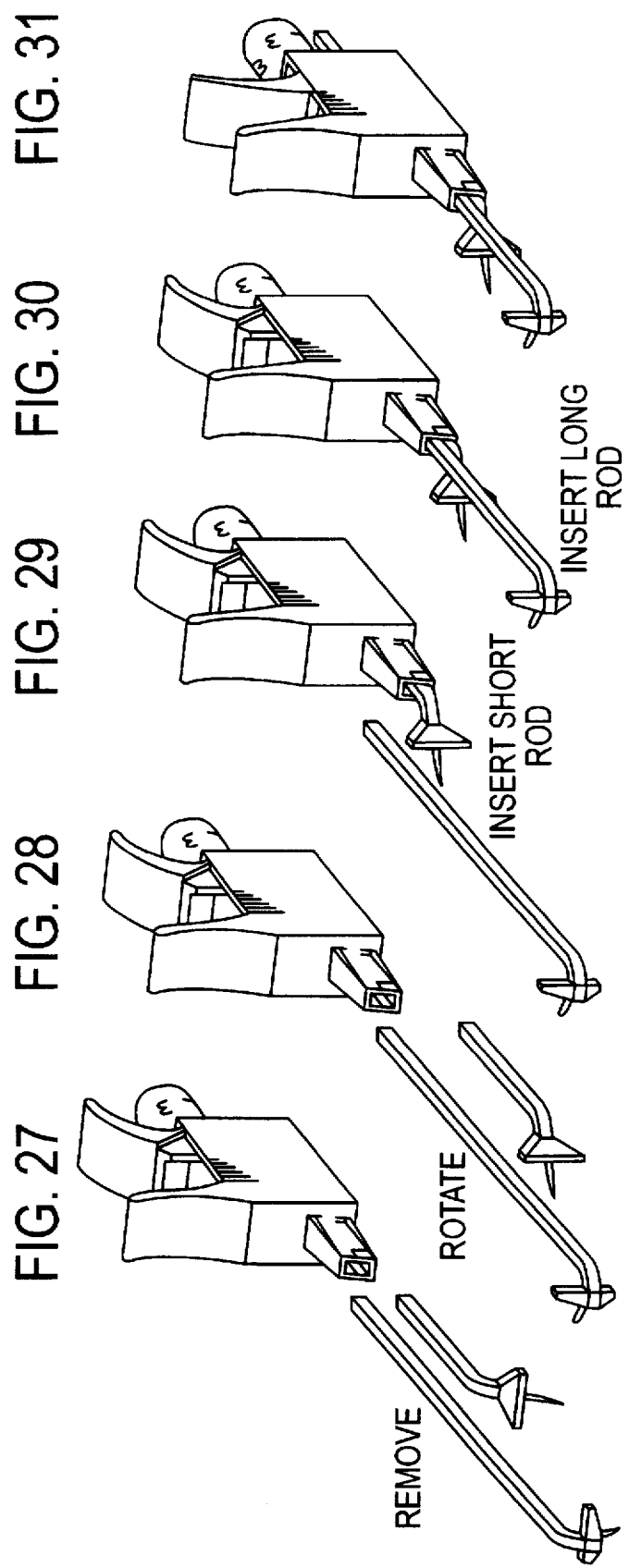

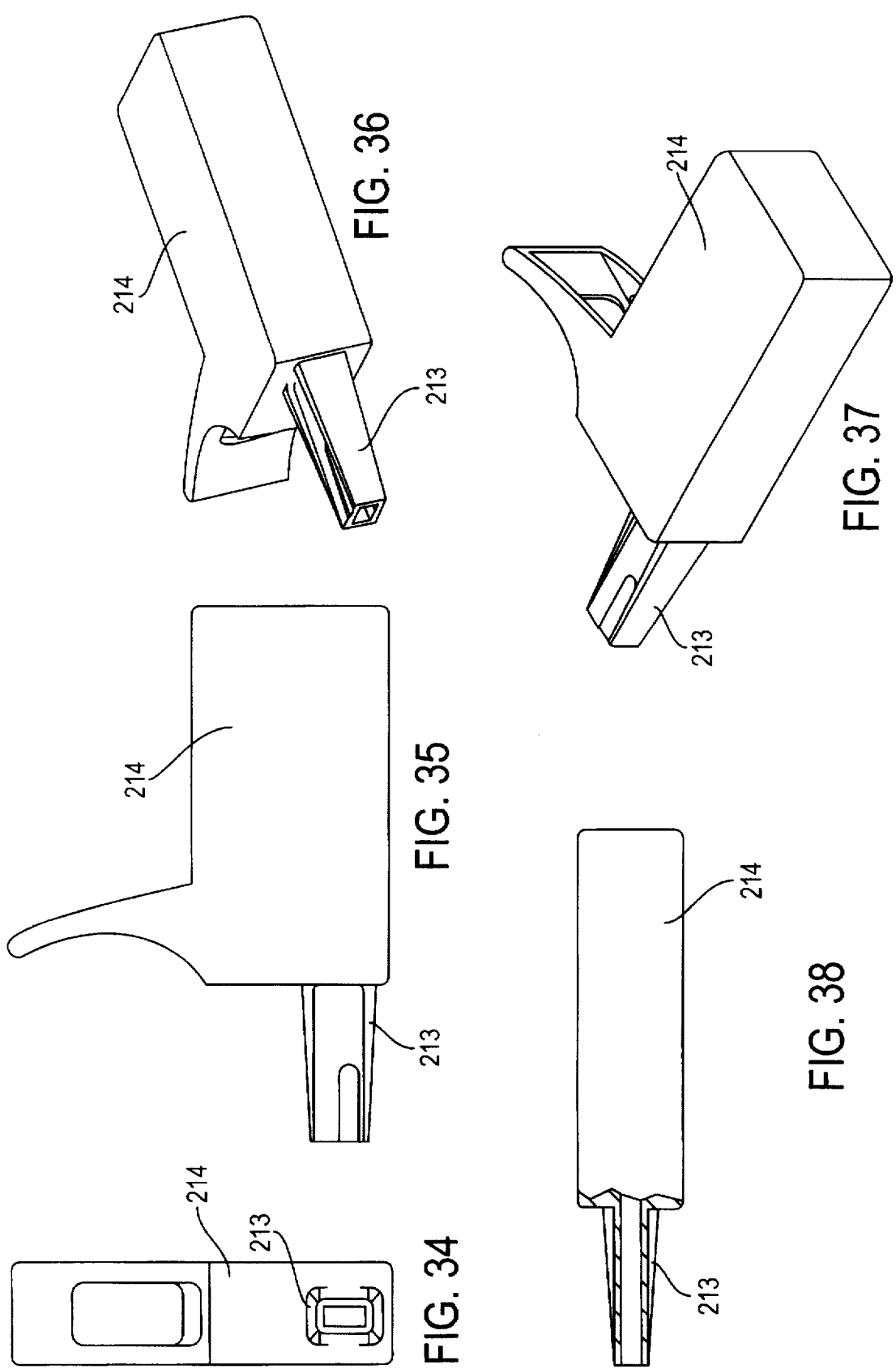

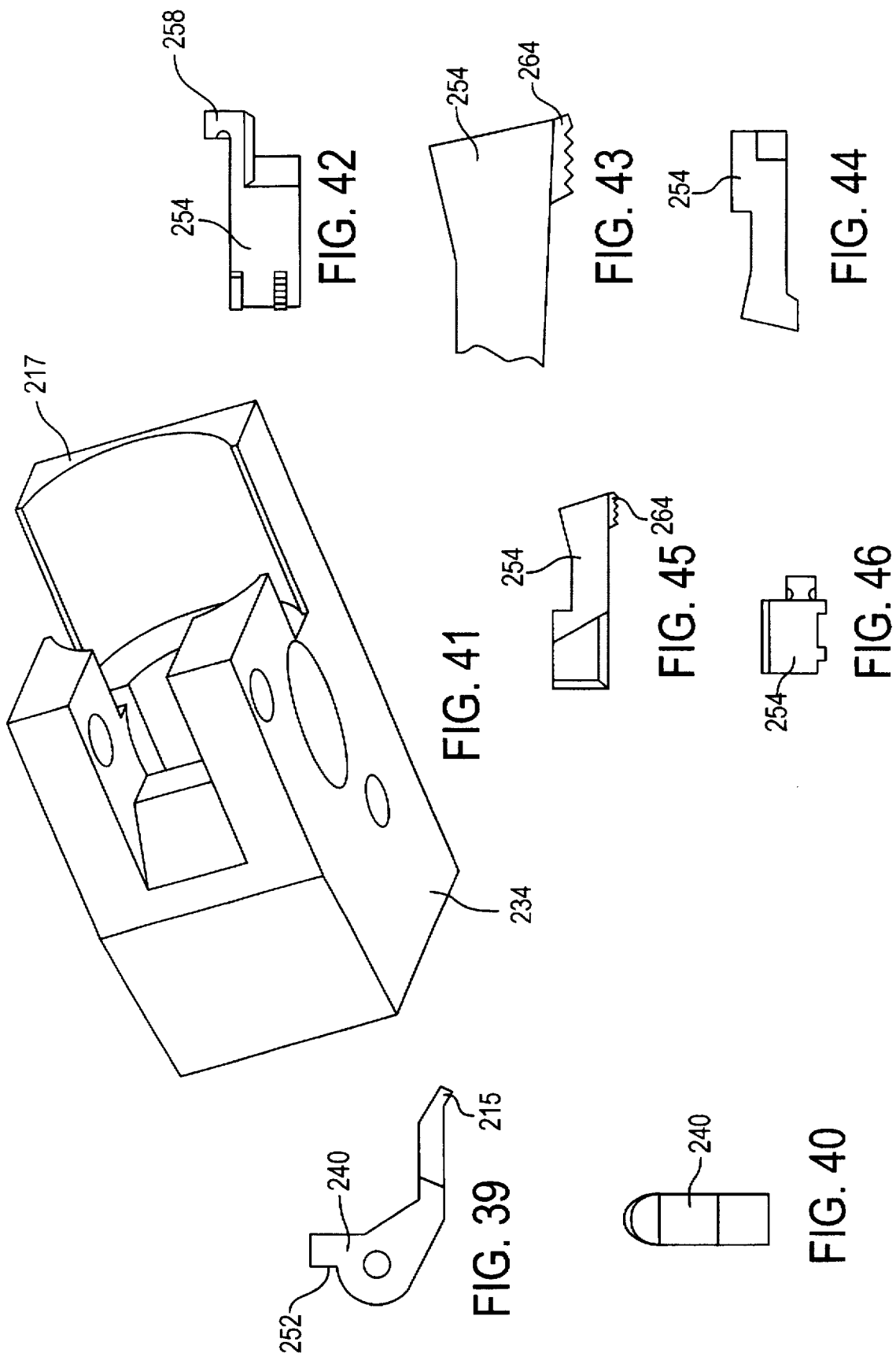

SINGLE NEEDLE SKIN STRETCHING DEVICE

This application is a continuation of application Ser. No. 08/230,931, filed Apr. 21, 1994, now abandoned.

BACKGROUND OF THE INVENTION

1. Field of the Invention

The invention relates to an apparatus for stretching skin to cover an open wound, and more particularly, to an apparatus for use before, during or after an operation for closure of skin defects or otherwise damaged skin areas.

2. Description of the Related Technology

U.S. Pat. No. 4,896,680 discloses a method and apparatus for stretching skin over a wound by load cycling. A force may be applied on opposite skin margins during several periods interrupted by relaxation periods, so skin may be stretched over a wide area. A surgical stretching apparatus according to that patent may include two pins for insertion into the skin along both edges of a wound.

The pins may be gradually pulled together by a flexible strap. The tension or pulling load on the pins may be applied in intervals to allow the collagen fibers of the skin to rearrange for further stretching. The pins may be substantially shaped as safety pins exhibiting a loop for attachment to a flexible strap. The strap may exhibit projections or apertures for engaging a ratchet-shaped device that may hold the pins in forceful apposition.

A disadvantage of the above-described apparatus is manifest when the pins have been drawn together, as no space or room is provided for suturing the approximated skin margins. Another drawback resides in the rather crude manner for approximating the pins, i.e., manually pulling on the flexible strap, as the pulling force cannot be minutely controlled.

There exists a need for a skin closing or skin stretching device that closes a skin defect in a single pulling operation. There further exists a need for a skin stretching apparatus that allows for suturing of the wound while the skin stretching apparatus remains situated about the wound. There is also a need for a skin stretching device where the surgeon can exercise incremental control over the applied closing force.

SUMMARY OF THE INVENTION

It is an object of the invention to provide a skin stretching or closing apparatus which permits suturing of skin edges while the stretching apparatus is in situ without disturbing the suturing operation.

It is another object of the invention to permit insertion into the wound margins of interdermal needles adapted to grip substantially the entire length of the wound and to permit the use of one or more stretching mechanisms distributed uniformly, or as required, along the length of the wound, thereby enabling the interdermal needles to be engaged in multiple locations.

It is a further object of the invention to provide a wound closing system employing skin stretching devices which provide a controlled incrementally actuated closing force to draw opposing skin edges toward one another.

One embodiment of a wound closing system may include two interdermal needles for insertion under skin along opposing edges of a wound to be closed and one or more skin stretching devices for approximating opposing edges of the wound. Each skin stretching device exhibits a pair of needle shafts each having a single hook at a distal end for engaging an interdermal needle, and a contracting mechanism provided for drawing the opposing needle hooks toward one another, thereby approximating the opposing margins of the wound. Because each skin stretching device exhibits only one needle hook on each side of the wound, alignment problems are minimized.

The number of skin stretching devices utilized in closing a particular wound ranges from one upward, and the devices may be distributed uniformly, or as required, along the length of the wound.

In an alternative embodiment, the skin stretching device exhibits a pivoting retaining member attached to each elongated shaft and exhibiting two or more skin insertion needles. The contracting mechanism draws the opposing needle hooks toward one another, thereby approximating the opposing margins of the wound.

In a third embodiment, the skin stretching device exhibits two shafts, the distal ends of which angle away from the body of the shafts. Each distal end exhibits a single skin piercing needle or hook. The contracting mechanism draws the opposing needles toward each other, thereby approximating the opposing margins of the wound.

In a fourth embodiment, the skin stretching device exhibits a long curved arm and a short curved arm, each exhibiting a single needle. The contracting mechanism draws the opposing margins of the wound together. This embodiment is particularly useful on curved body parts, such as arms, legs, skulls, torsos and other curved areas of the body.

BRIEF DESCRIPTION OF THE DRAWINGS

FIG. 12 shows a side view of a longer shaft of the device shown in FIG. 10.

FIG. 13 shows a side view of a shorter shaft of the device shown in FIG. 10.

FIG. 14 shows a front end view of the shorter needle shown in FIG. 13.

FIG. 15 shows a perspective view of the knob cover of the device shown in FIG. 10.

FIG. 16 shows a perspective view of the knob cover of the device shown in FIG. 15 in a slightly rotated position.

FIG. 17 shows a perspective view of the knob cover of the device shown in FIG. 16 in a further rotated position.

FIG. 18 shows a perspective view of the knob cover of the device shown in FIG. 17 in a further rotated position.

FIG. 19 shows a perspective view of the knob cover of the device shown in FIG. 18 in a further rotated position.

FIG. 20 shows a perspective view of the knob cover of the device shown in FIG. 19 in a further rotated position.

FIG. 21 shows a cross section view of the knob cover of the device shown in FIG. 10.

FIG. 27 shows a perspective view of the device shown in FIG. 10 with both shafts detached from the housing.

FIG. 28 shows a perspective view of the device shown in FIG. 27 with both shafts rotated to an alternate position.

FIG. 29 shows a perspective view of the device shown in FIGS. 27–28 with the shorter shaft inserted into the contracting mechanism.

FIG. 30 shows a perspective view of the device shown in FIGS. 27–29 with the shorter shaft inserted and the longer shaft partially inserted.

FIG. 31 shows a perspective view of the device shown in FIGS. 27–30 with both shafts fully inserted.

FIG. 34 shows a front view in elevation of the housing shown in FIG. 32.

FIG. 35 shows a side view in elevation of an alternative embodiment of the housing surrounding the contracting mechanism.

FIG. 36 shows a front perspective view of an alternative embodiment of the housing shown in FIG. 35.

FIG. 37 shows a rear perspective view of the housing shown in FIG. 35. FIG. 38 shows the bottom plan view of the housing shown in FIG. 35.

FIG. 39 shows a side view of the pawl of the device shown in FIG. 10.

FIG. 40 shows a bottom plan view of the pawl shown in FIG. 39.

FIG. 41 shows a perspective view of the slider block of the device shown in FIG. 10.

FIG. 42 shows a bottom view the wedge of the device shown in FIG. 10.

FIG. 43 shows a partial side view of the wedge shown in FIG. 42.

FIG. 44 shows a right side view the wedge shown in FIGS. 42–43.

FIG. 45 shows a left side view of the wedge shown in FIGS. 42–44.

FIG. 46 shows an end view of the wedge shown in FIGS. 42–45.

DETAILED DESCRIPTION OF THE PREFERRED EMBODIMENT

Figure 1:
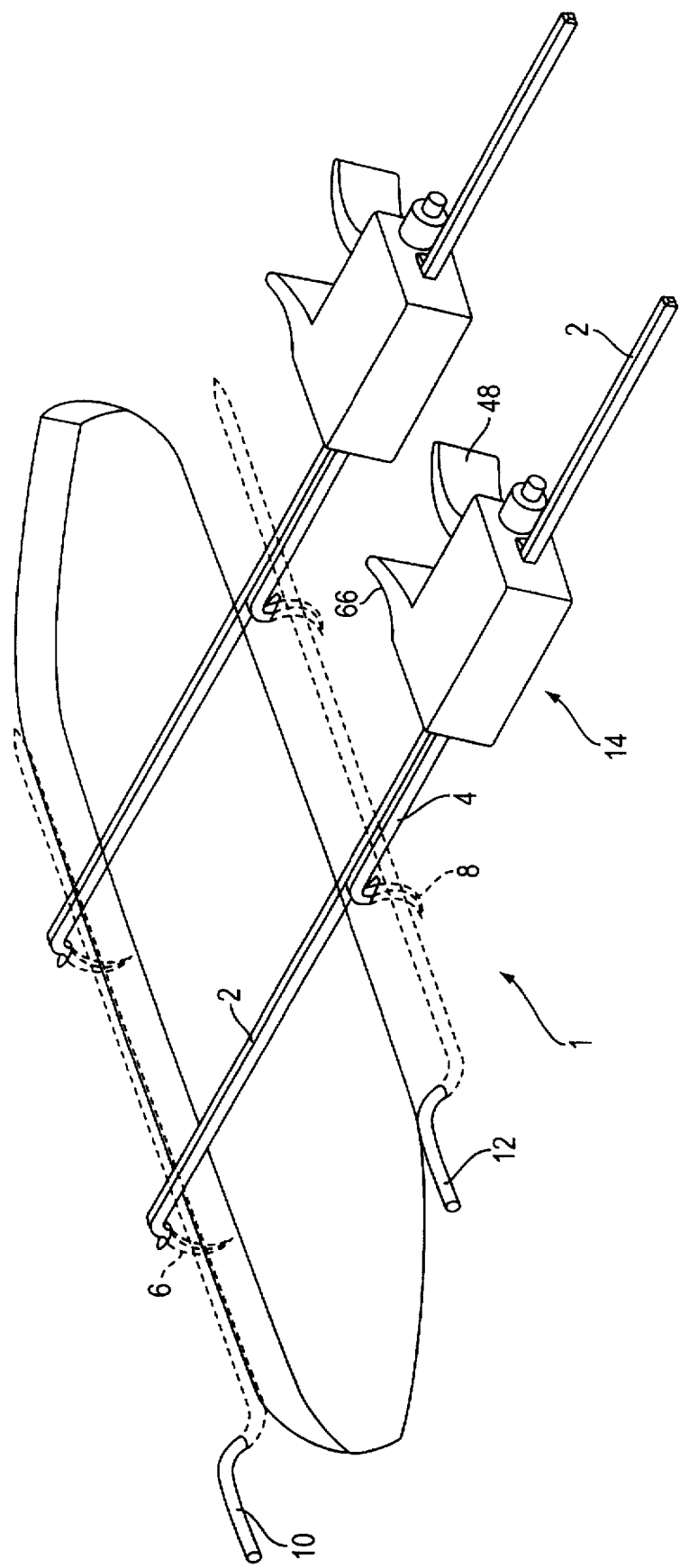
FIG. 1 shows a perspective view of two single needle skin stretching devices according to a first embodiment of the invention positioned over an open skin wound.

With reference to the embodiment shown in FIGS. 1 through 6, one or more skin stretching devices 1 may be used with one or more interdermal needles 10, 12, which may be inserted under the skin along the wound margins as shown in FIG. 1. Each skin stretching device may include a pair of needle shafts 2, 4 exhibiting needle hooks 6, 8 respectively, for engaging the interdermal needles.

The needle shafts 2, 4 may be removably inserted into a contracting mechanism 14 of the skin stretching device 1, and may be inserted in several angular positions about an axis of the needle shaft, thereby allowing the contracting mechanism 14 to lie at different angles with respect to the skin surface. The needle shafts 2, 4 in the first embodiment may exhibit a square cross-section, which allows the contracting mechanism to be arranged in varying positions. Alternatively, the needle shafts may exhibit a cross-section of a different geometry, such as rectangular, octagonal, hexagonal or circular. According to another preferred configuration, needle shafts having a rectangular cross-section are provided using an out of square ratio sufficient to force the tool to be arranged in either a right handed or left handed position.

According to the embodiment shown in FIG. 1, the contracting body is arranged in parallel with the surface of the skin. If the tool shown in FIG. 1 is considered to be a right handed tool, a left handed tool is created by reinstalling the needles 180 degrees from the position shown. The needles shown in FIGS. 3 through 6 may be rotated 90 degrees from the position shown in FIG. 1 so that the contracting mechanism may be perpendicular to the skin surface.

The needle shafts may be of any desired length which is sufficient to span the wound. The device may exhibit relatively short needle shafts whereby the contracting mechanism is located in close proximity to the wound site. Alternatively, the device may exhibit long needle shafts, thereby allowing the contracting mechanism to be located remote from the wound site. When long shaft lengths are desired, one or more shaft-to-shaft stabilizing collars (not shown) may be provided about the needle shafts 2 and 4 to maintain alignment with one another.

According to the first embodiment, the skin stretching device exhibits a needle shaft 2, which is relatively longer, and a needle shaft 4, which is relatively shorter. Both the long needle shaft and the short needle shaft are inserted into a stepped bore 16 in the contracting mechanism. The cross-sectional shape of the stepped bore 16 corresponds to the cross-sectional shape of the needle shafts 2 and 4. A first end of the short needle shaft 4 exhibits a needle hook 8, and a second end of the short needle shaft abuts a stepped portion or shoulder 18 in the stepped bore 16. The needle shaft 4 is held in the stepped bore by friction fit or a retaining spring. According to another embodiment, an alternate shaft coupled to a strap (not shown) may be inserted into the stepped bore. This alternate shaft could be bent, if desired, to reach a suitable attachment.

A first end of the long needle shaft 2 exhibits a needle hook 6. The long needle shaft 2 extends through the stepped bore, and a second end thereof protrudes from a remote side of the contracting mechanism. The outer surfaces of needle shaft 2 may be smooth, or may exhibit a knurled, ridged or toothed surface, which would allow it to be gripped by the contracting mechanism and propelled in controlled increments by limited spring forces.

Figure 2:
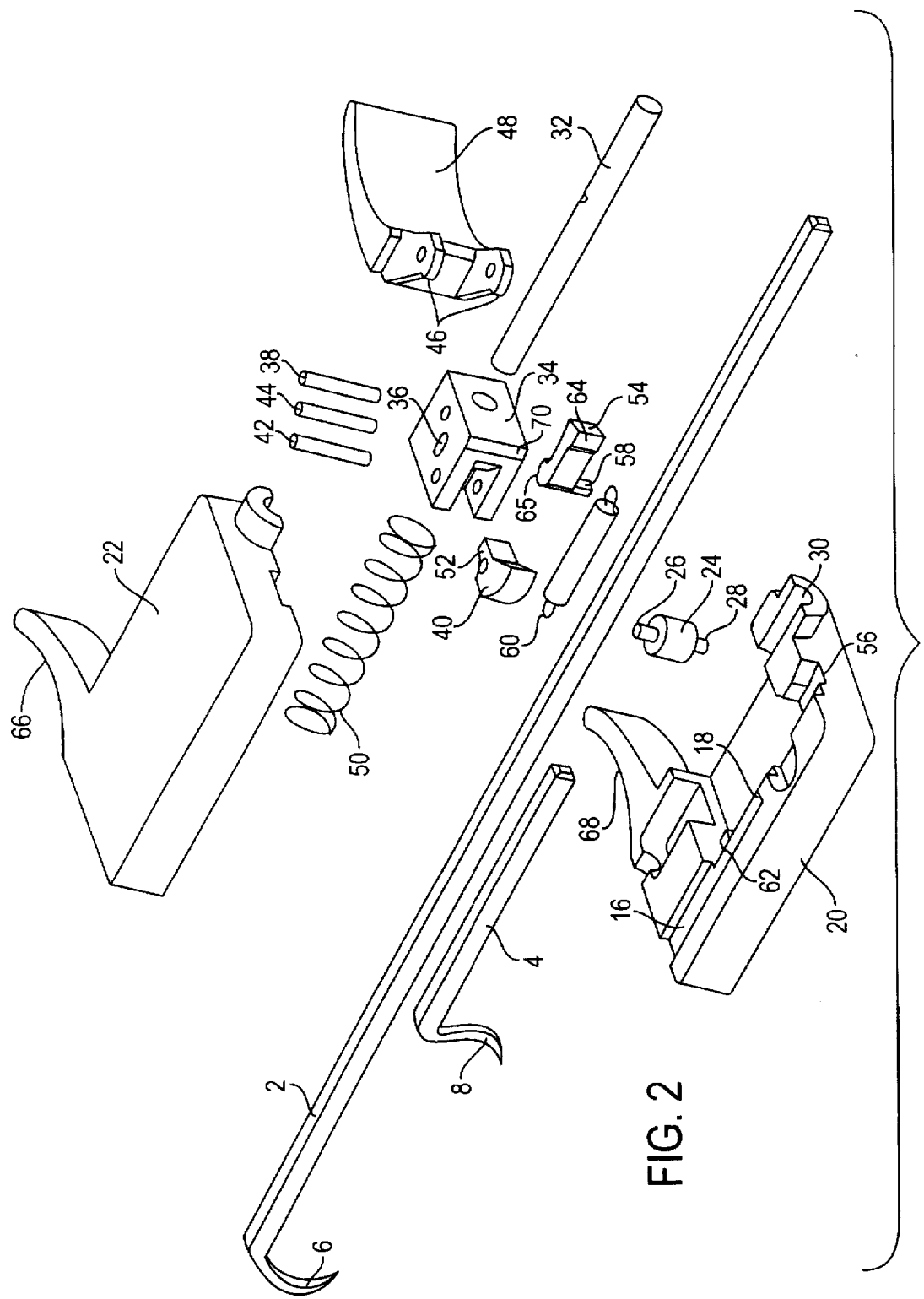
FIG. 2 shows an exploded perspective view of one of the single needle skin stretching devices shown in FIG. 1.

FIG. 2 shows the construction and assembly of the contracting mechanism according to the first embodiment of the invention. The outer casing of the contracting mechanism includes two casing halves 20 and 22, which are joined together by any conventional means, such as bonding, ultrasonic welding, screws, rivets or snap fits. Alignment/press pins (not shown) may also be used in joining the casing halves together. A one-piece roller 24 may be used, which pivots on pin extensions 26 and 28, is disposed within the outer casing. Each casing half 20 and 22 exhibits an internal hole (not shown) in which the pin extensions 26 and 28 are guided. The roller 24 helps minimize the friction between needle shaft 2 and the outer casing of the contracting mechanism.

A second longitudinal bore 30 is provided in the casing of the contracting mechanism for slidably receiving a slide pin 32. The slide pin also passes through a longitudinal bore in a slider block 34 and is fixedly secured to the slider block by pin 38 which passes through and transverse bores in both the slider block and the slide pin.

A pawl 40 projects from a bottom portion of the slider block and is pivotally secured into the slider block by pin 42. The end of the pawl 40 which engages the longer needle shaft 2 may exhibit a smooth, knurled or toothed surface. A cross pin 44 is inserted through an elongated slot 36 in the slider block 34 and couples motion between a lower end 46 of a thumb grip 48 and the pawl 40.

A main spring 50 is disposed within the housing of the contracting mechanism. A first end of the spring 50 abuts an internal wall at a forward portion of the contracting mechanism casing. A second end of spring 50 abuts the slider block 34 and an upwardly extending lever 52 of pawl 40. The main spring 50 exerts a force on the slider block 34 allowing the slider block to fully extend upon release of the thumb grip. The main spring 50 also exerts a force on pawl 40, which in turn exerts a driving force on the needle shaft 2, upon release of the thumb trigger, for drawing opposing hooks 6 and 8 toward one another.

A wedge 54 is disposed within a recess 56 at the rear portion of the contracting mechanism housing. The recess 56 prevents the wedge 54 from becoming dislocated when the needle shaft 2 is removed from the stepped bore 16. A portion of the wedge 54 includes a post 58 which is coupled to one end of an extension spring 60. The other end of extension spring 60 is coupled to a post 62 which protrudes from an inner wall of casing half 20. The extension spring exerts a pulling force on the wedge 54 which exerts a greater force on the needle shaft 2 due to the mechanical advantage of the cam surface 64 thereby preventing the needle shaft from backing up. The cam surface 64 of the wedge 54 may exhibit a smooth, knurled or toothed surface for engaging a surface of the needle shaft 2.

The thumb grip 48 is pivotally attached at its lower end 46 to the slider block 34 by pin 38. The outer casing halves 20, 22 of the contracting mechanism is provided with a corresponding finger grip halves 66, 68. The use of terms "finger grip" and "thumb grip" merely imply a preferred usage. The grips can clearly be used in other ways, such as in a reverse manner.

The skin stretching device is contemplated for use in closing wounds or skin defects. After excising the margins of the wound to be closed, the surgeon inserts the two interdermal needles 10 and 12 into the skin along opposing margins of the wound.

Next, if necessary, the needle shafts 2 and 4 may be removed from the contracting mechanism 14 and reinserted in the desired angular orientation. With the thumb grip 48 in the release position (FIG. 6), the long needle shaft 2 is longitudinally displaced to the desired position for insertion about the wound. The needle hooks 6 and 8 are then inserted into the skin along the margins of the wound to engage the interdermal needles 10 and 12, respectively.

Figure 3:
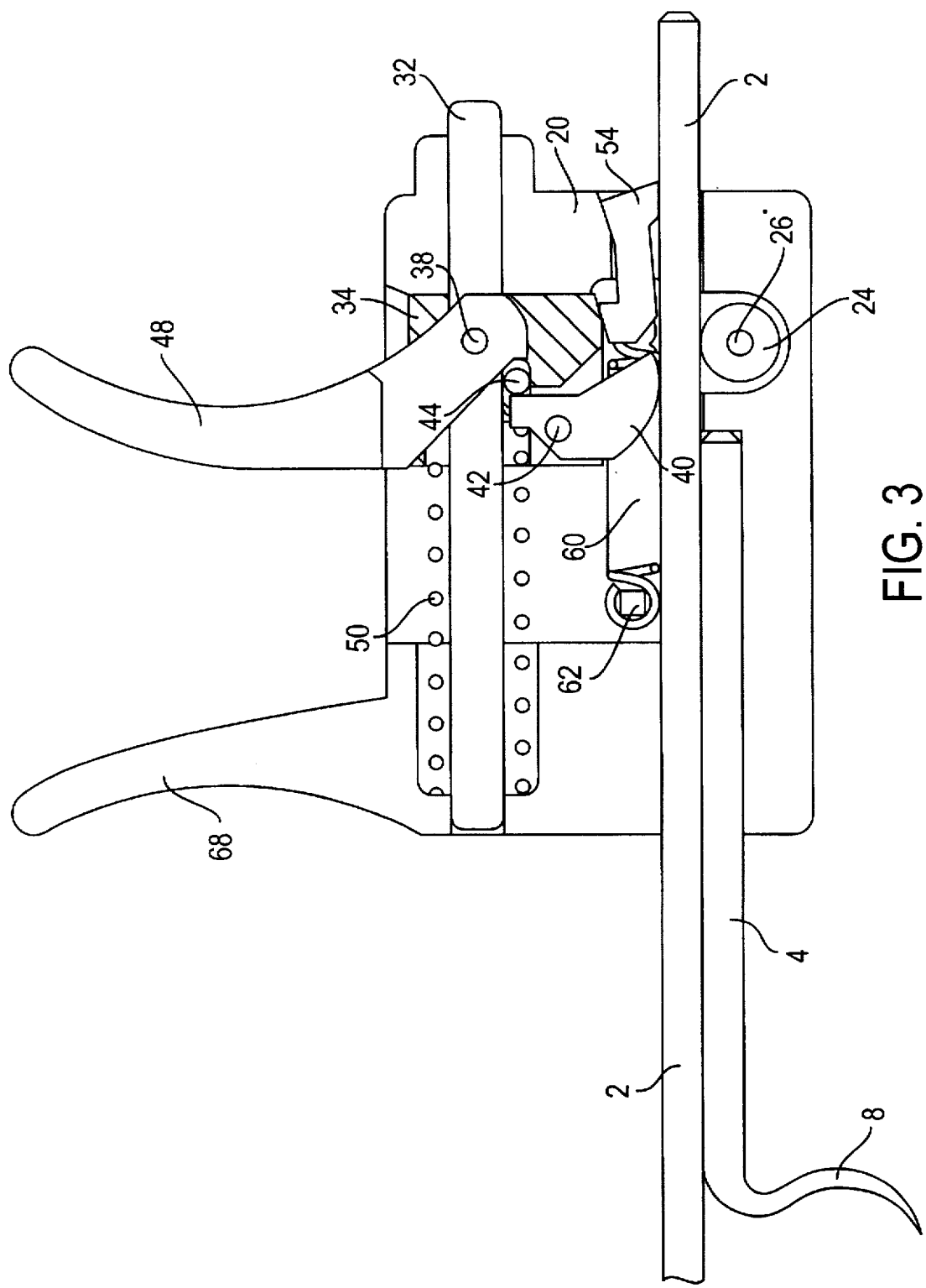
FIG. 3 shows a sectional side view in elevation of one of the single needle skin stretching devices of FIG. 1 shown in a relaxed position.

Once the needle hooks have engaged the interdermal needles, the thumb grip 48 is moved to the engaged position as shown in FIG. 3. When the thumb grip 48 is in the upright, engaged position, the pawl 40 is pivoted about its pivot pin 42 and spring loaded against the needle shaft 2 by a force exerted by main spring 50. The extension spring 60 exerts a force on the wedge 54, gently forcing the wedge between the housing 20 and the needle shaft 2, thereby preventing the needle shaft 2 from backing up due to the opposing force exerted on the device by the skin.

The device is actuated by squeezing the thumb grip 48 toward the finger grip 66, 68 and immediately releasing the grips. This actuation may be repeated, as necessary to draw needles 6 and 8 closer to one another by propelling the long needle shaft 2 through the contracting mechanism. The rate at which the needles are drawn together is determined by the natural action of the skin stretching in response to the restoring force of the calibrated internal spring.

As described in U.S. Pat. No. 4,896,680, a skin closing operation may be performed in several stages to allow the skin to stretch in a gradual manner during intervals between the stretching stages. After the skin defect or wound margins have been brought into contact, the wound may be sutured in a manner known to the art, whereby it is evident that needle shafts 2 and 4 do not interfere with the operation.

Figure 4:
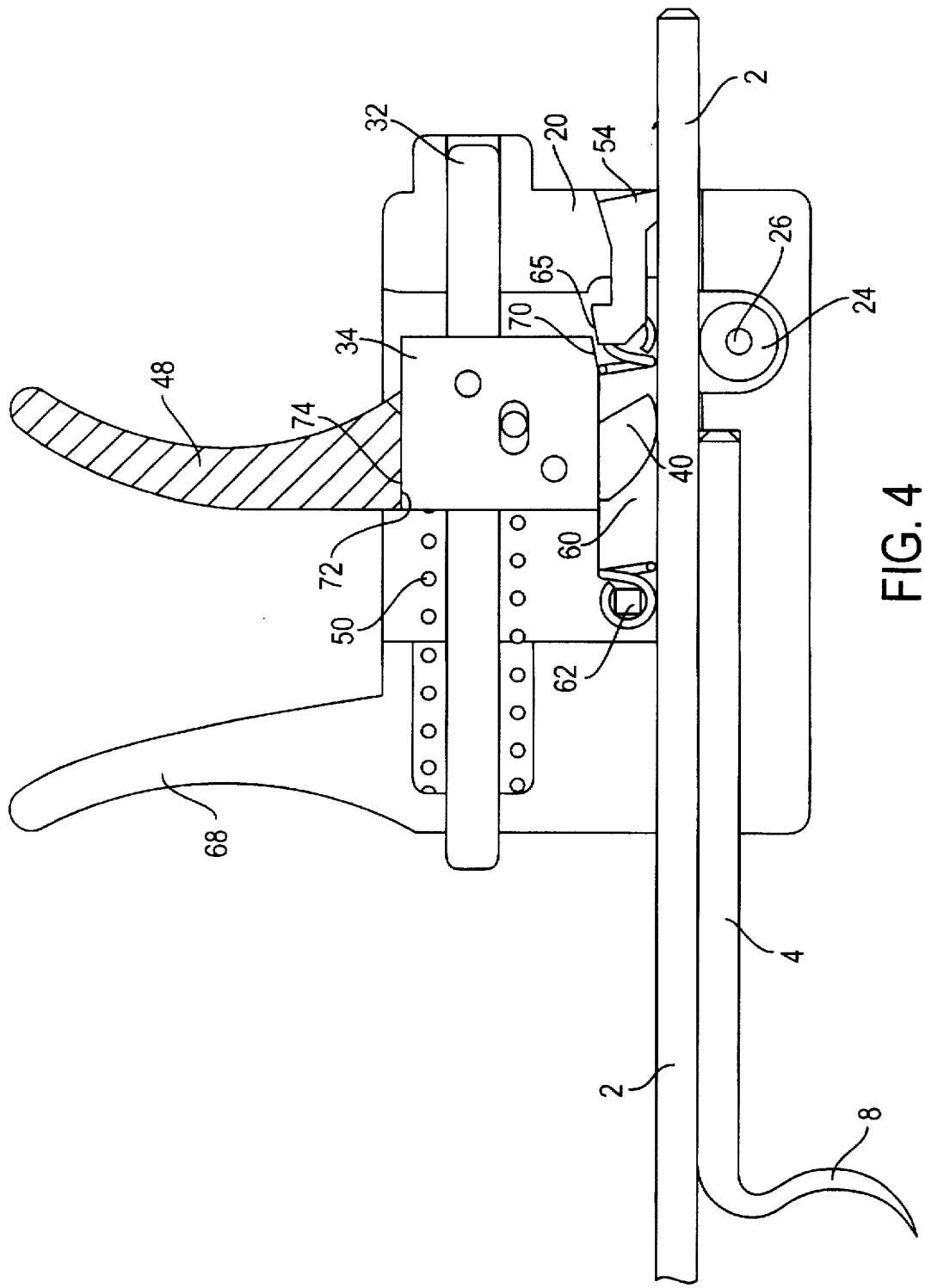
FIG. 4 shows a sectional side view in elevation of one of the single needle skin stretching devices of FIG. 1 shown in a partially actuated position.

As shown in FIG. 4, the thumb grip 48 is pivoted until shoulder 72 is in abutment with the upper surface 74 of the slider block 34. When thumb grip 48 is actuated toward the finger grip 66, the slider block 34 with the slide pin 32 displaces the pawl 40 along the needle shaft 2 as the main spring 50 is compressed, while the wedge maintains the position of the needle shaft 2.

Figure 5:
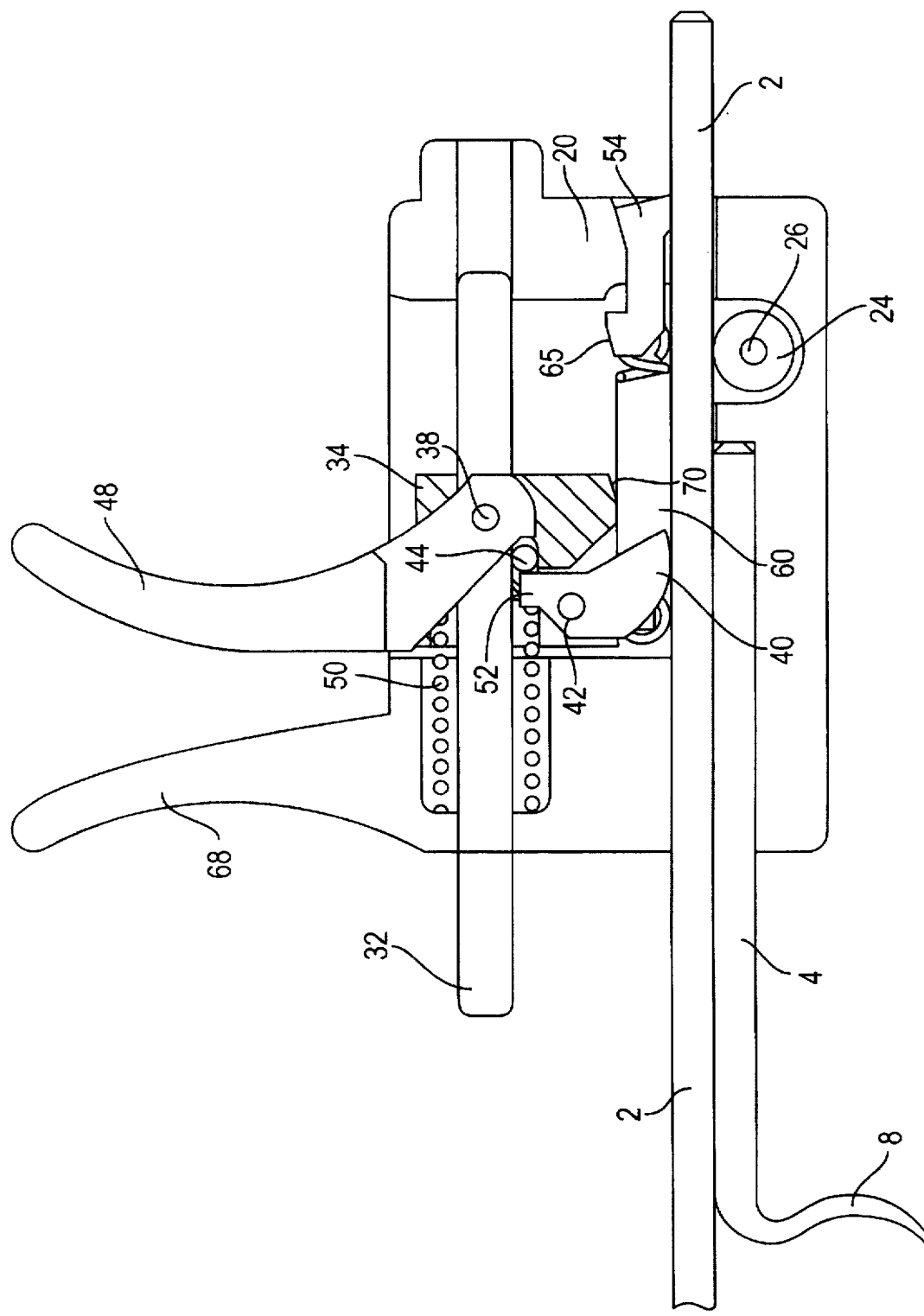
FIG. 5 shows a sectional side view in elevation of one of the single needle skin stretching devices of FIG. 1 shown in a fully actuated position.
Figure 10:
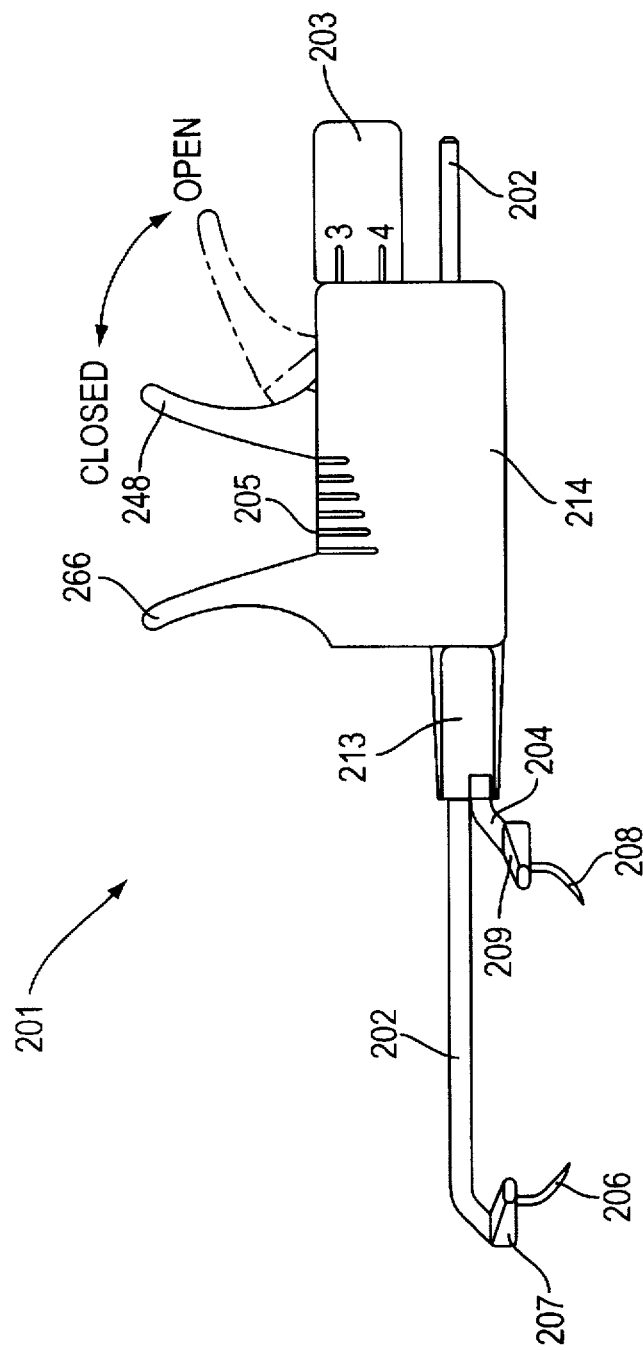
FIG. 10 shows a side view in elevation of a wound closing device according to a third embodiment.
Figure 11:
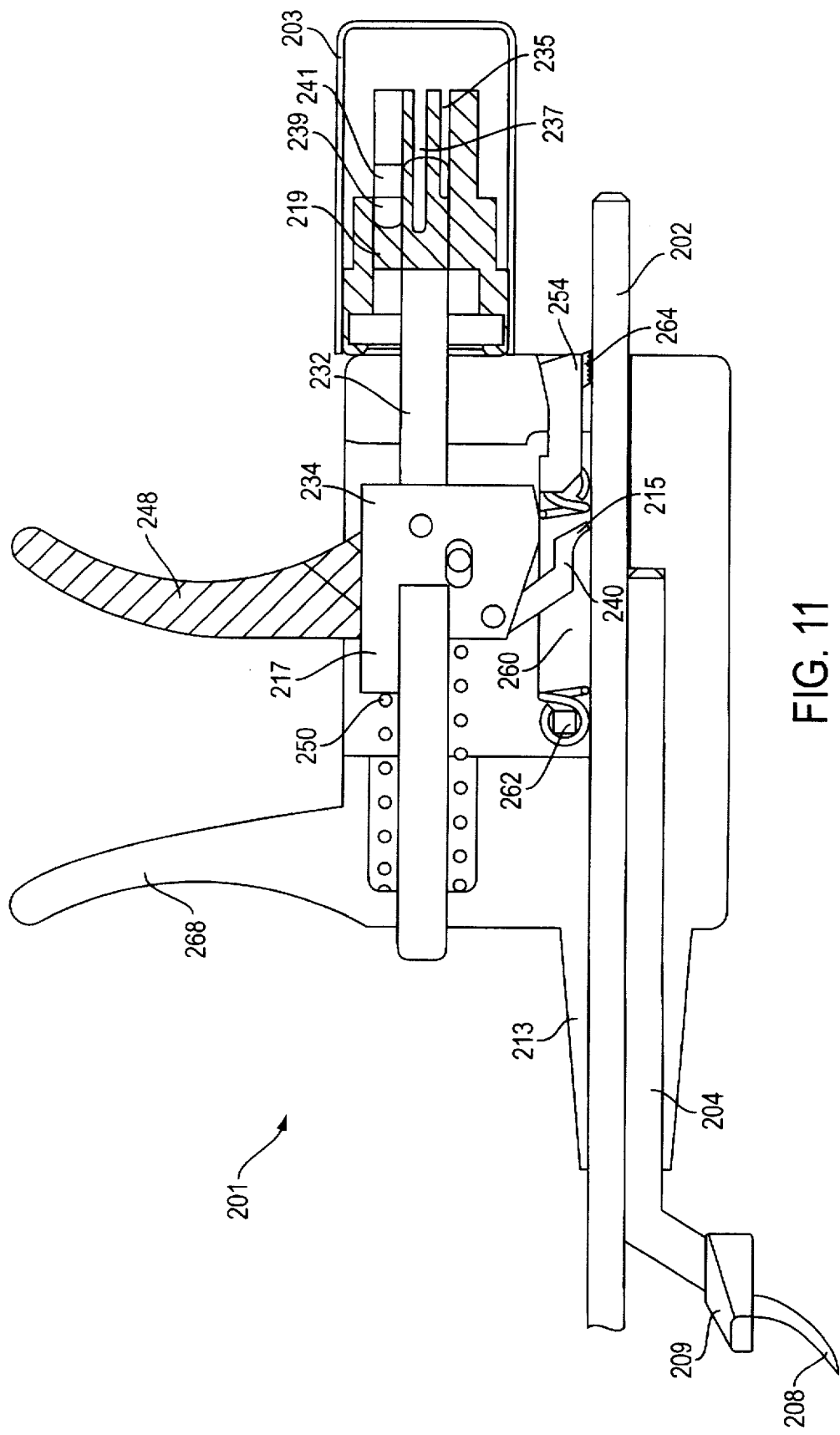
FIG. 11 shows a sectional side view in elevation of the device shown in FIG. 10.
Figure 24:
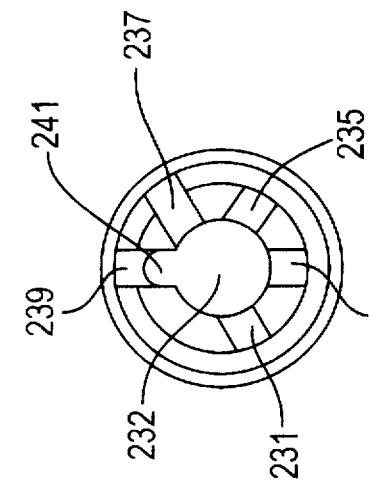
FIG. 24 shows a front sectional view of the knob of the device shown in FIG. 10.
Figure 23:
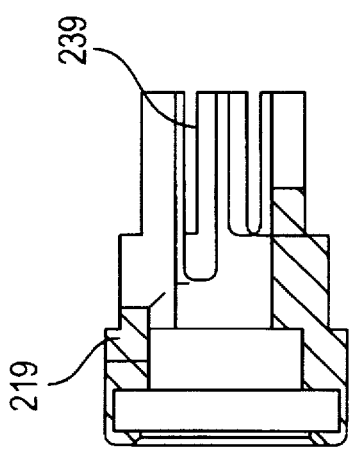
FIG. 23 shows a side sectional view of the knob of the device shown in FIG. 10.
Figure 22:
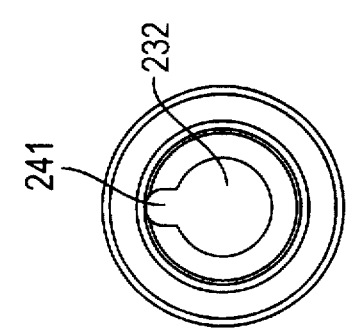
FIG. 22 shows a front end view of a knob of the device shown in FIG. 10.
Figure 25:
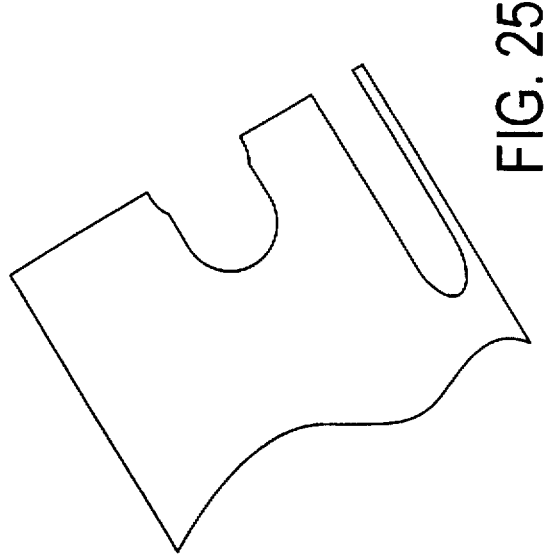
FIG. 25 shows an enlarged side view of a portion of the knob of the device shown in FIG. 23.
Figure 26:
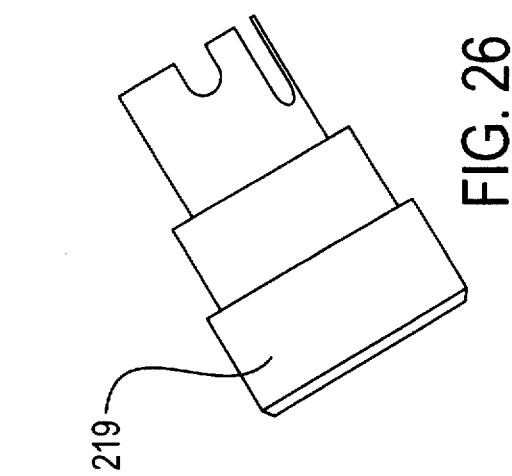
FIG. 26 shows a side perspective view of the knob of the device shown in FIG. 10.
Figure 33:
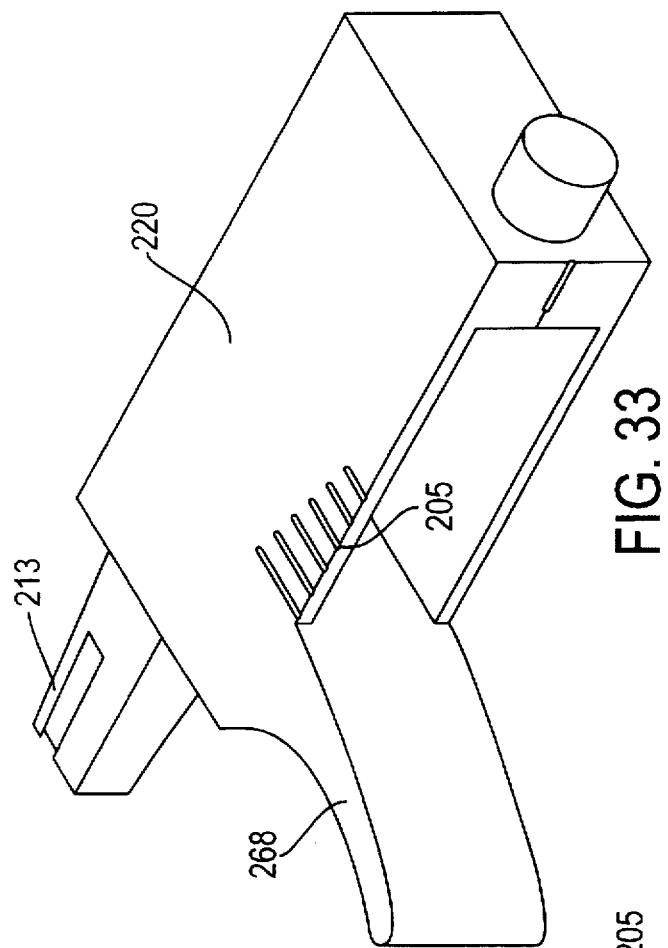
FIG. 33 shows a top rear perspective view of the housing of the device shown in FIG. 10.
Figure 32:
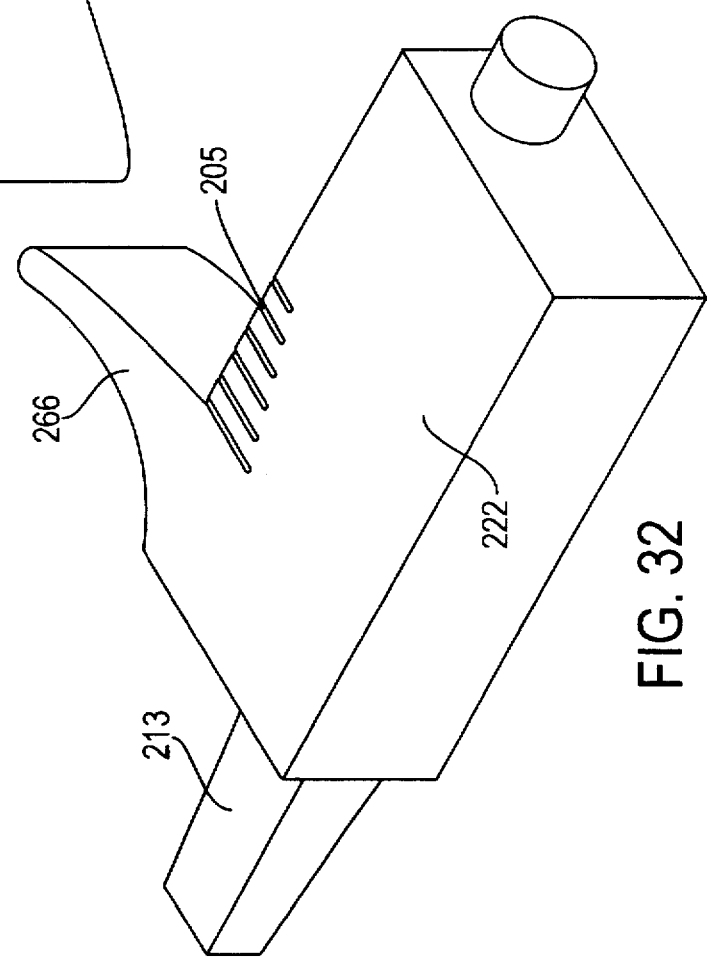
FIG. 32 shows a bottom rear perspective view of the housing of the device shown in FIG. 10.

Once the thumb grip is actuated toward the finger grip, as shown in FIG. 5, the main spring 50 is compressed to a pre-determined maximum tension. The tension may be controlled and reduced by a tension limiting knob 203 (see FIGS. 10-33), which interacts with the main spring and the slider block to limit the tension exerted upon the pawl, which in turn, limits the driving force exerted upon the needle shaft. The force applied to the wound margins may be seen on a tension indicator 205, as best shown in FIG. 10.

An operator squeezes the thumb grip and the finger grip which compresses the spring 50. Upon release of the grip, a balanced force is applied to the main spring 50 which exerts a force on the slider block 34, which in turn exerts a pressure on the pawl 40. The pawl engages needle shaft 2 by striking a non-slip wedging angle with a surface thereof, and acts as a one-way driving mechanism to apply the force exerted by the main spring to propel the needle shaft 2. The non-slip wedging action may be assisted by the knurled, toothed or smooth surface of the needle shaft 2. In this manner, the pawl drives the needle shaft 2 as a ratchet and rack. The main spring 50 also exerts a force directly upon the upwardly extending lever 52 of pawl 40, thereby providing a restoring torque to the pawl about its pivot point 42.

Figure 6:
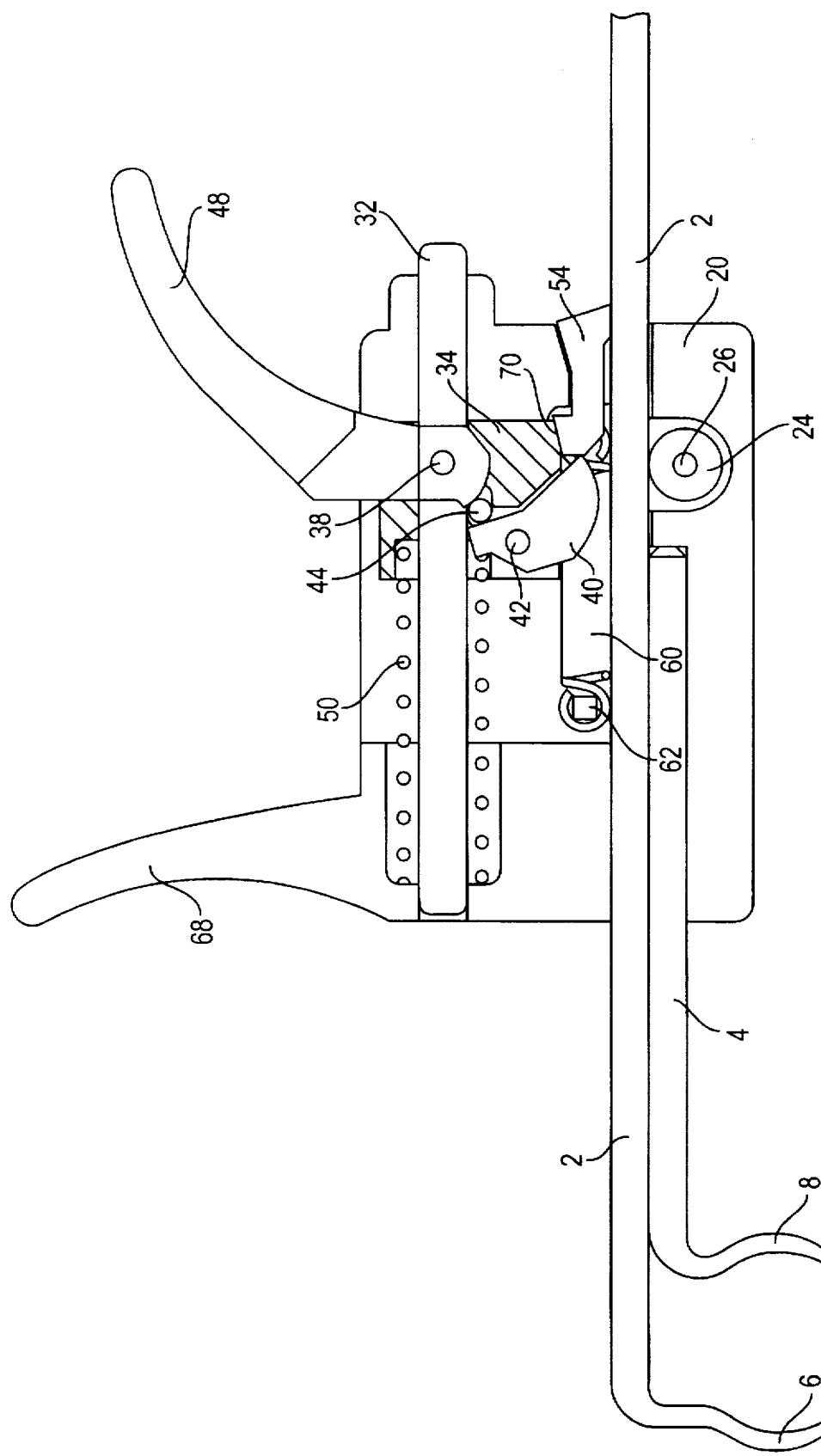
FIG. 6 shows a sectional side elevational view of the body of the single needle skin stretching device of FIG. 1 shown in a released position.

As shown in its most rearward position in FIG. 6, the skin stretching device is released by rotating the thumb grip 48 to its released position. This forces the cross pin 44 against the pawl 40 causing it to rotate about its pivot point 42 and engage the wedge 54. Thumb grip 48 can be rotated to the release position at any displacement position in the tool operating cycle, such as from the fully displaced position shown in FIG. 5. Upon rotating the thumb grip 48, the pawl is disengaged from needle shaft 2 allowing the main spring 50 to fully extend and displace the slider block 34 to its fully extended position. The main spring 50 exerts a much greater force than the contracting force exerted by the extension spring 60. Consequently, the wedge 54 is longitudinally displaced causing it to release the anti-backup hold exerted on the needle shaft 2. To assure that the pawl properly displaces the wedge, a ramp area 70 of slider block 34 engages a ramp area 65 of the wedge to apply lever action vertically to the wedge as the slider block approaches its fully extended position. This is used to unseat the wedge from a possible locking condition (severe static friction) it may encounter due to resistance from a heavy back-force on the needle. The unseating overcomes any friction, but does not adversely affect the anti-backup action of the wedge.

With both the pawl 40 and wedge 54 disengaged from the needle shaft 2, the needles 6 and 8 no longer exert a significant force on the margins of the wound. In the release position, needle shafts 2 and 4 may be freely displaced along their respective longitudinal axes, or removed entirely from the contracting mechanism. The release position is utilized at the beginning of the operation to facilitate insertion of the needle hooks into the skin, and at the end of the operation, after suturing, to facilitate removal of the hooks.

Figure 7:
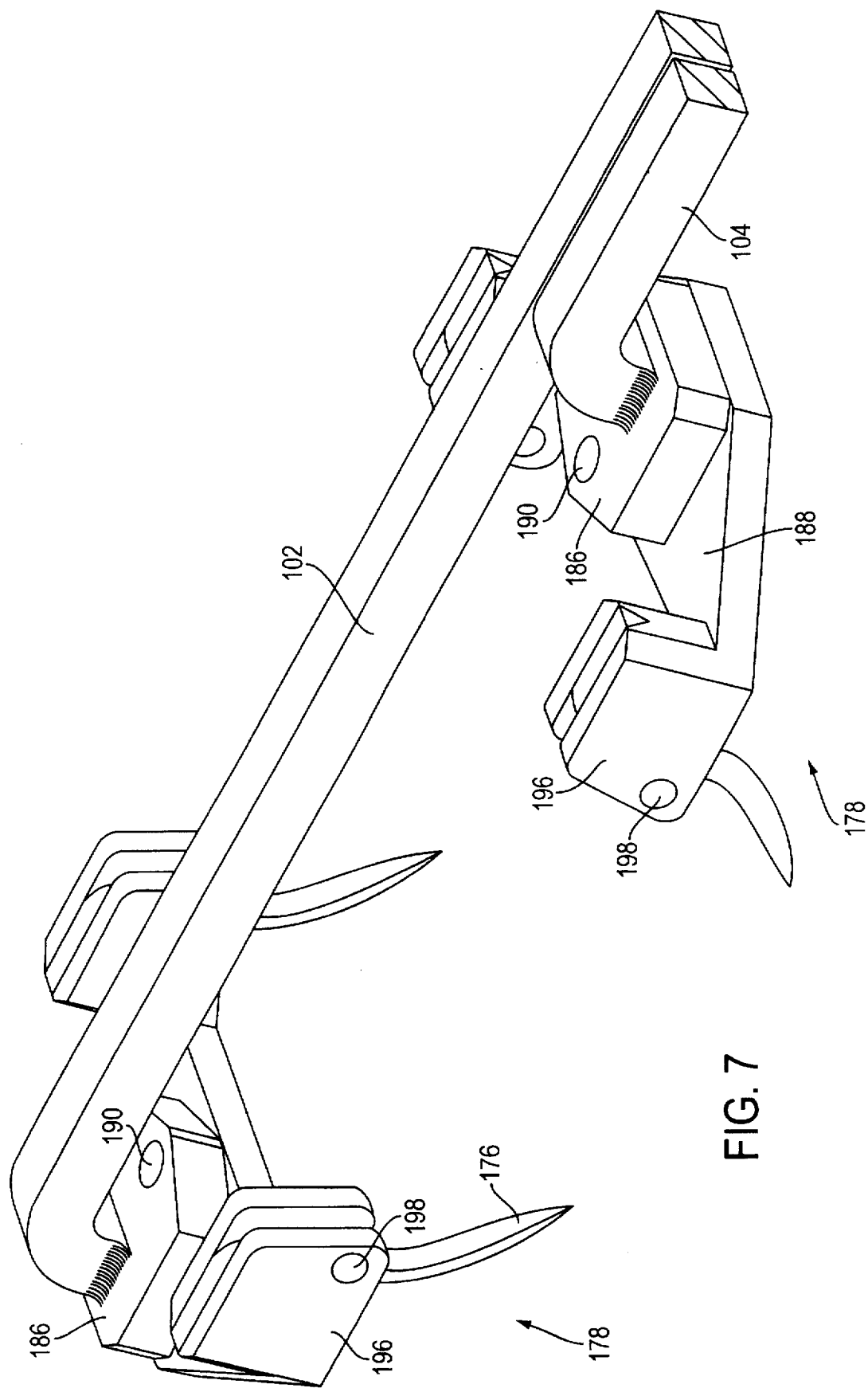
FIG. 7 shows an enlarged perspective view of the retaining members of a skin stretching device according to a second embodiment of the invention.
Figure 8:
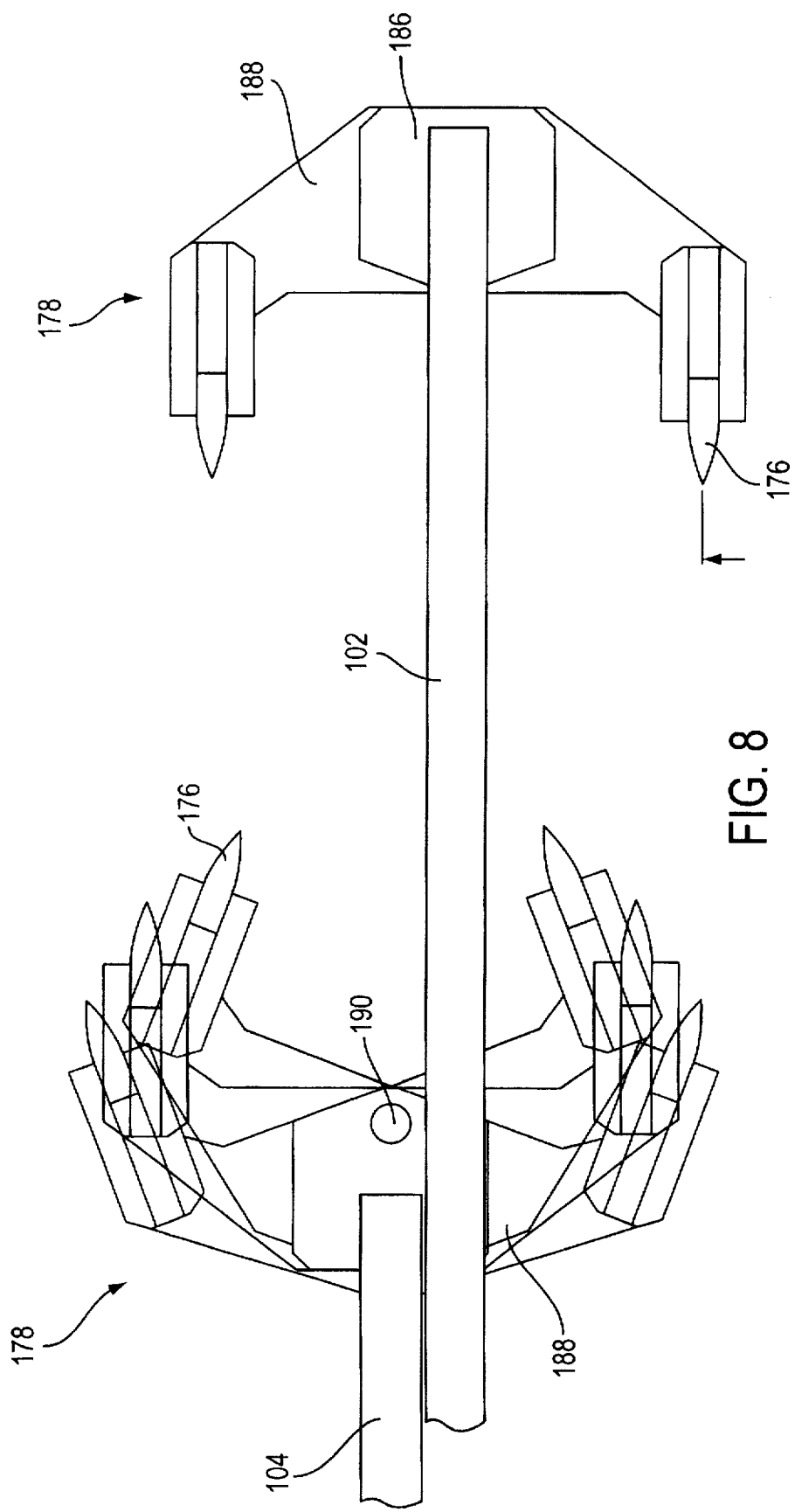
FIG. 8 shows a top plan view of the embodiment shown in FIG. 7.
Figure 9:
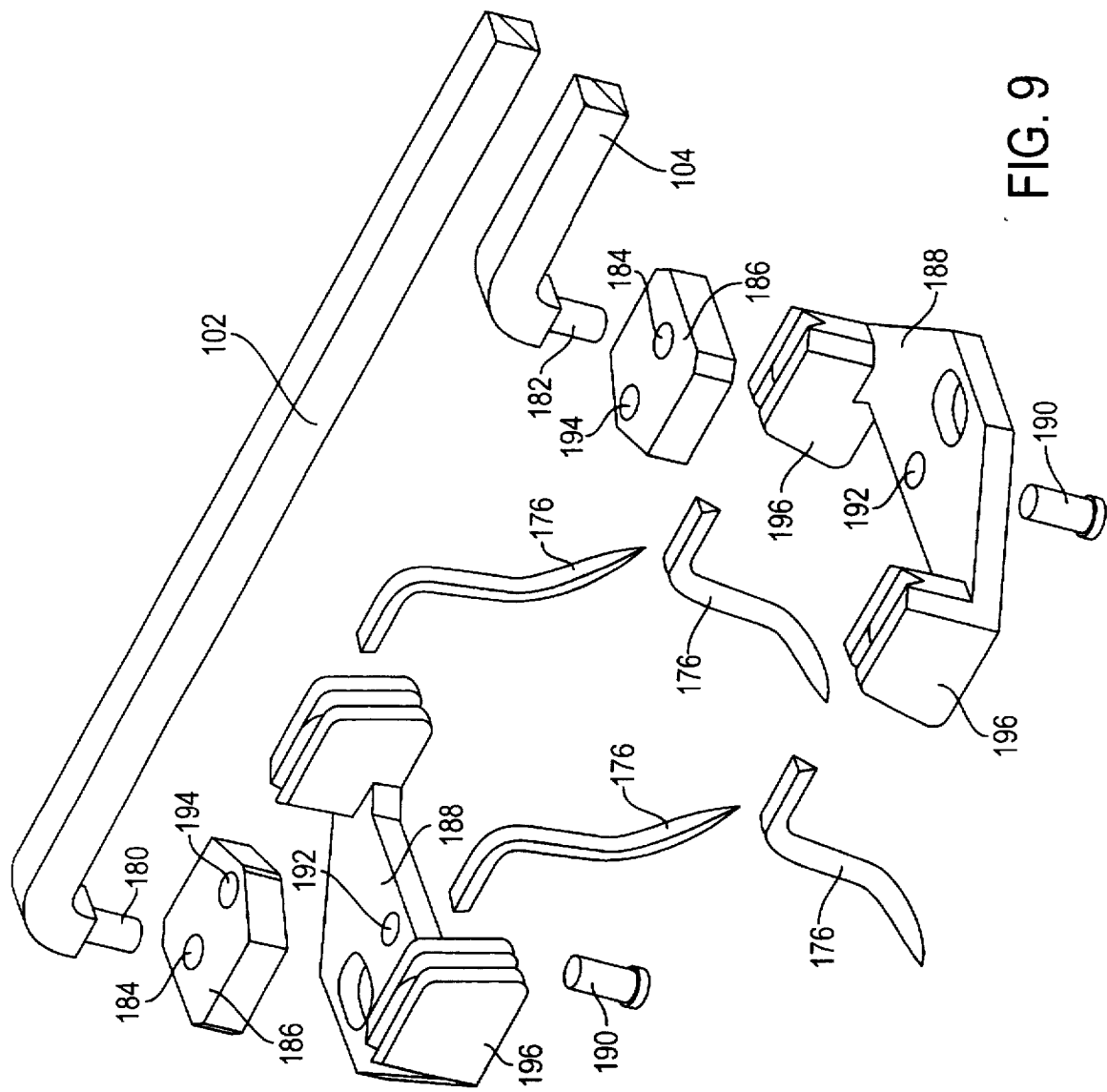
FIG. 9 shows an exploded perspective view of the embodiment shown in FIG. 7.

FIGS. 7 through 9 show a portion of a wound closing device according to a second embodiment. According to this embodiment, the distal end of each elongated shaft 102, 104 exhibits a pivotal retaining member 178, each carrying a plurality of skin insertion elements 176. According to the preferred configuration of the second embodiment, each shaft 102, 104 exhibits a pin 180, 182 at its distal end attaching it to a retaining member 178 through a bore 184 in an upper fixed plate 186 of the retaining member. Each upper fixed plate 186 is pivotally connected to a swivel platform 188 by a pivot pin 190 which inserts through a bore 192 in the swivel platform 128 and a bore 194 in the fixed plate 186. As best seen in FIG. 7, the swivel platform 188 exhibits flanges 196 at lateral ends thereof. Each flange 196 exhibits a skin insertion needle 176 anchored thereto by a pin 198. The advantage of this embodiment is that it provides flexibility in closing odd shaped wounds, especially wounds where the edges are not parallel.

FIGS. 10–46 show a skin stretching device 201 according to a third embodiment of the invention. The skin stretching device 201 is substantially similar to the skin stretching device of the first embodiment, wherein like reference numerals indicate like components. In addition to the components shown in the first embodiment, the skin stretching device according to the third embodiment includes a control knob 203 for limiting the amount of force applied by the device, and a tension indicator 205 for indicating the amount of force applied by the device.

According to the preferred configuration, the skin stretching device 201 of the third embodiment includes a long needle shaft 202 and a short needle shaft 204, each of which is removably inserted into a contracting mechanism 214. Distal ends of the shafts 202, 204 angle away from the body of shafts 202, 204, and exhibit retaining members 207, 209 to which the skin insertion needles 206, 208 are attached. The angled distal ends allow a space to exist wherein sutures can be sewed, and the retaining members 207, 209 provide lateral stability for the skin stretching device 201. The outer surfaces of the longer needle shaft 202 preferably exhibit a ridged or toothed surface 211, as shown in FIG. 12, which allow it to be gripped by the contracting mechanism and propelled in controlled increments by limited spring forces.

The housing for the contracting mechanism 214 exhibits a flange 213 on its front surface of which surrounds at least a portion of the shafts 202, 204. The housing 214 also exhibits a lever 266, 268 integral to the surface of the housing of the contract mechanism, and a movable lever 248 to which force is applied to activate the contracting mechanism in the same manner described in the first embodiment.

A longitudinal bore is provided in the casing of the contracting mechanism for slidably receiving a slide pin 232. The slide pin also passes through a longitudinal bore in a slider block 234 and is fixedly secured to the slider block by pin which passes through transverse bores in both the slider block and the slide pin.

A pawl 240 projects from a bottom portion of the slider block and is pivotally secured into the slider block by a pin. The pawl 240 according to the third embodiment exhibits a tooth 215 which engages the ridged or toothed surface 211 of the longer needle shaft 202. A cross pin is inserted through an elongated slot in the slider block 234 and couples motion between a lower end of the thumb grip 248 and the pawl 240.

A main spring 250 is disposed within the housing of the contracting mechanism. A first end of the spring 250 abuts an internal wall at a forward portion of the contracting mechanism casing. A second end of spring 250 abuts the slider block 234 and an upwardly extending lever 252 of pawl 240. The slider block 234 may include an extended flange portion 217 to prevent lateral deflection of the spring 250 and/or to limit the longitudinal travel of the slider block. The main spring 250 exerts a force on the slider block 234 allowing the slider block to fully extend upon release of the thumb grip. The main spring 250 also exerts a force on pawl 240, which in turn exerts a driving force on the needle shaft 202, upon release of the thumb trigger, for drawing opposing hooks 206 and 208 toward one another.

A wedge 254 is disposed within a recess at the rear portion of the contracting mechanism housing. The wedge includes a post 219 which is coupled to one end of an extension spring 260. The other end of extension spring 260 is coupled to a post 262 which protrudes from an inner wall of casing half 220. The extension spring exerts a pulling force on the wedge 254 which exerts a greater force on the needle shaft 202 due to the mechanical advantage of the cam surface 264, thereby preventing the needle shaft from backing up. According to the preferred embodiment, the cam surface 264 of the wedge 254 exhibits a toothed surface for engaging the ridged or toothed surface 211 of the needle shaft 202.

The skin stretching device according to the third embodiment also exhibits a knob comprising an external knob cover 203 and an internal knob element 219. The knob controls the tension applied by the contracting mechanism 214 and is situated on the rear side of the contracting mechanism. As shown in FIGS. 15–21, the external knob casing 203 exhibits a plurality of different settings 221, 223, 225, 227 and 229. The operator of the device may select a setting depending on the size and location of the wound. Each setting 221, 223, 225, 227 and 229 on the external knob casing 203 corresponds to an internal notch 231, 233, 235, 237 and 239 formed in a surface of the internal knob element 219. Each internal notch exhibits a different longitudinal length. The internal knob element exhibits a central bore which surrounds the slider pin 232. The distal end of the slider pin 232 exhibits a lug 241 which is selectively received by one of the notches 231, 233, 235, 237 and 239 of the internal knob element 219. The length of the selected notch limits the distance which the thumb lever can be compressed by restricting the longitudinal travel of the slider pin 232. By rotating the knob 203 to one of the plurality of settings 221, 223, 235, 237 or 239, the operator controls the extent which the thumb lever 248 may be compressed. Settings corresponding to the longer longitudinal recesses, such as 239, allow the thumb lever 248 to be fully or nearly fully compressed, whereas the shorter longitudinal recesses, such as 231, prevent the thumb lever from being fully compressed.

FIGS. 32–38 show a housing for a contracting mechanism according to a further embodiment.

Figure 47:
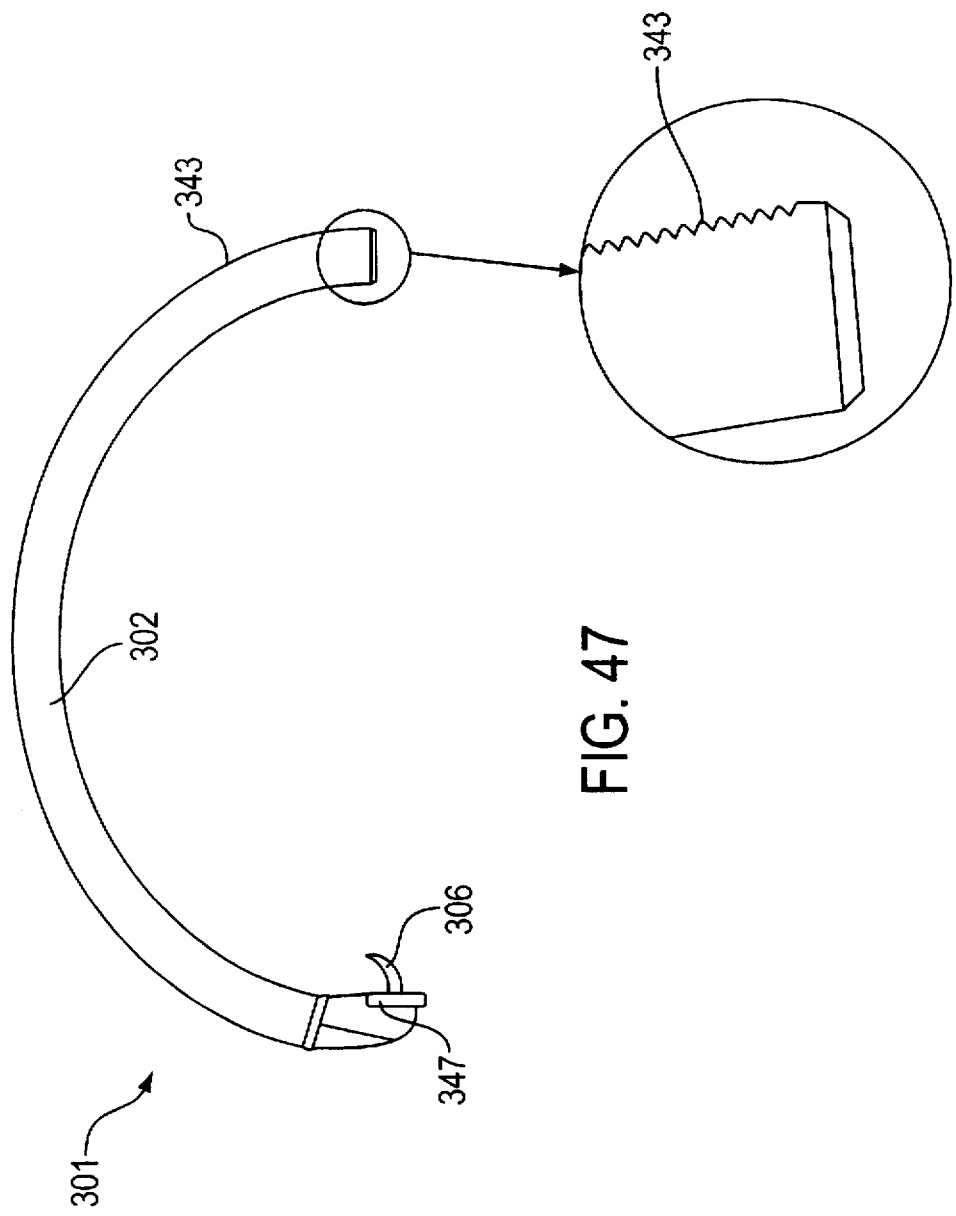
FIG. 47 shows a side a view of a contracting arm according to a fourth embodiment of the invention.
Figure 48:
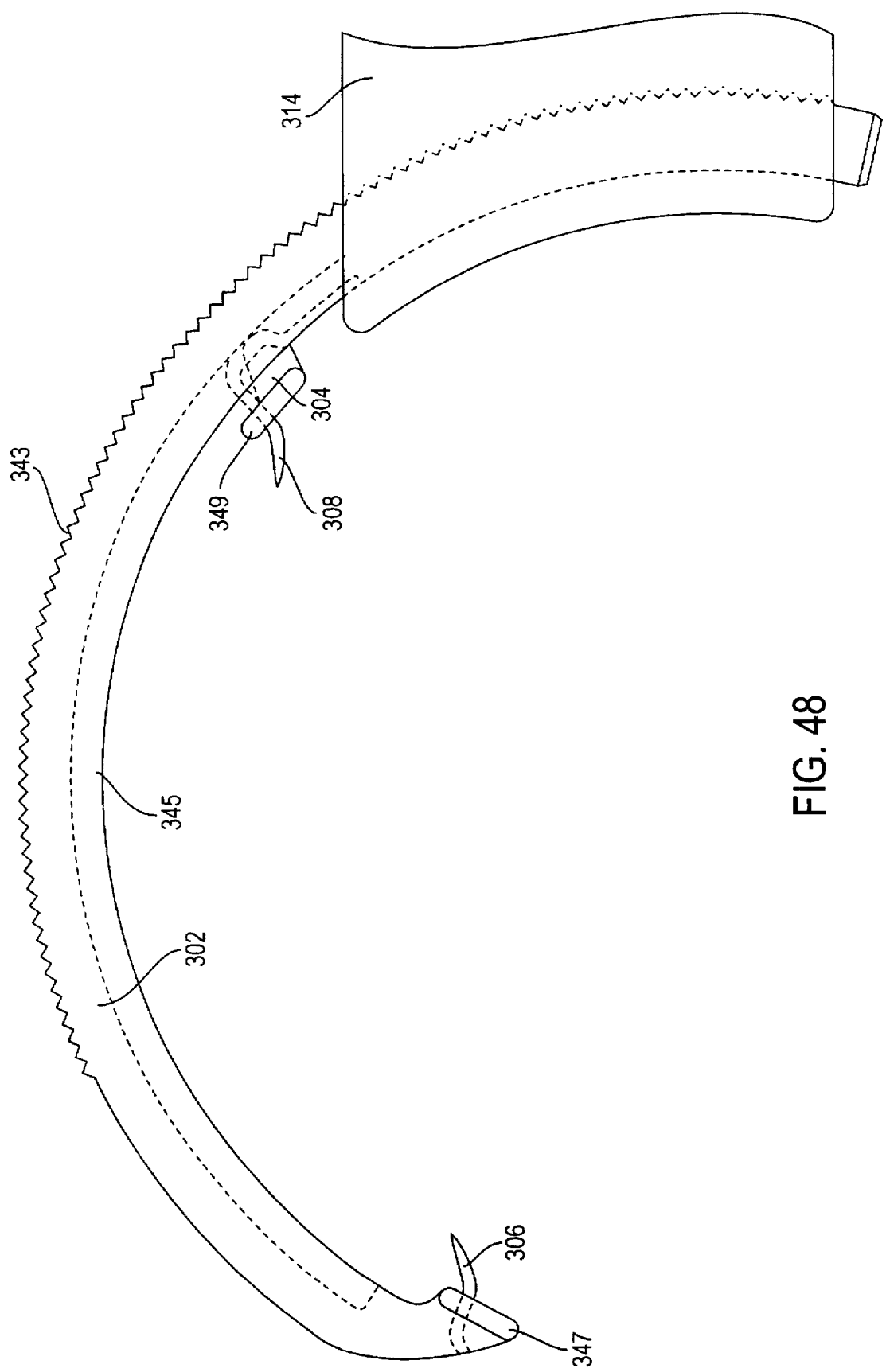
FIG. 48 shows an enlarged side view of the contracting arm of the fourth embodiment of the device shown in FIG. 47.
Figure 49:
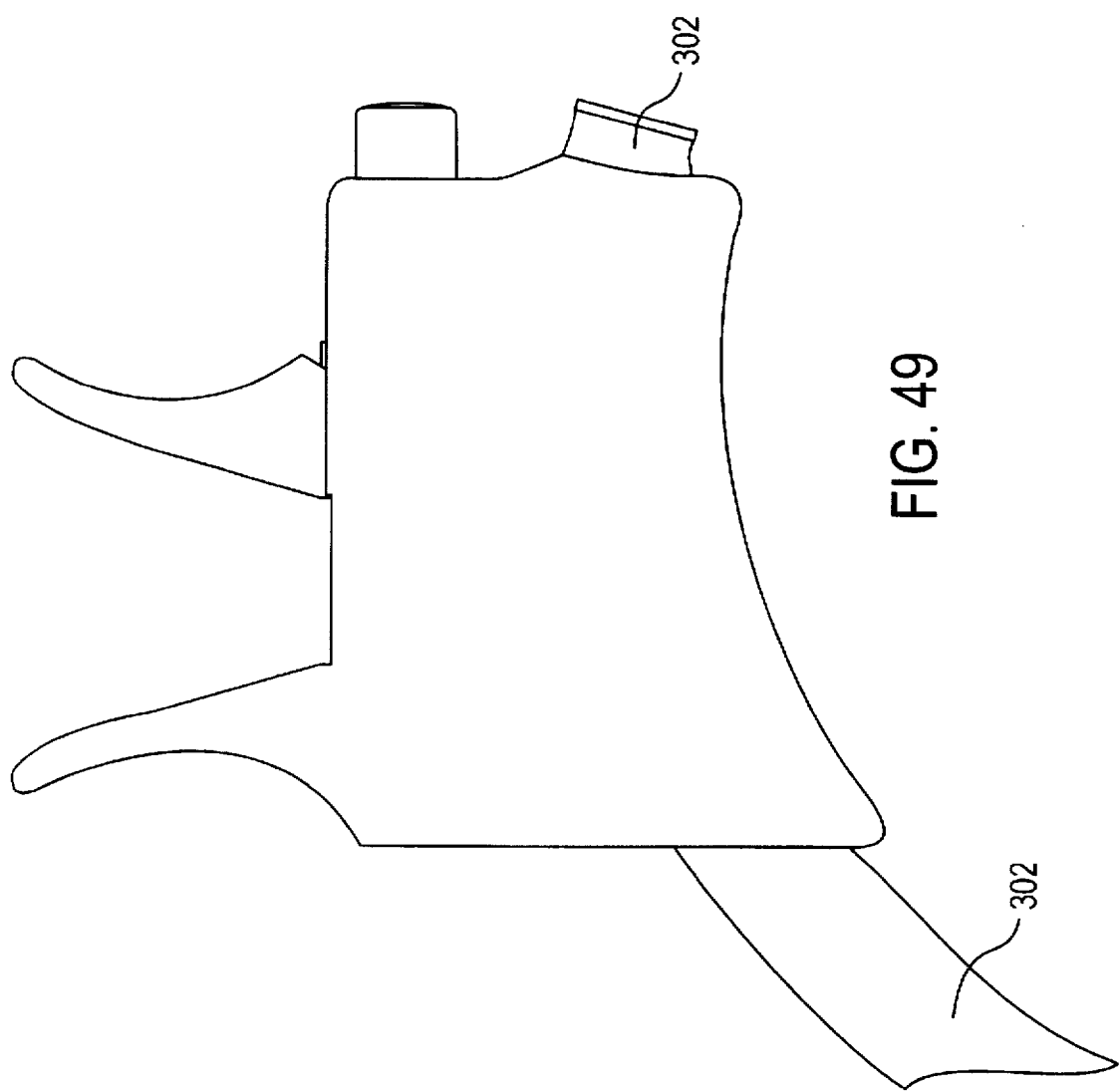
FIG. 49 shows a side view of the contracting mechanism according to a fourth embodiment of the invention.

FIGS. 47–49 show a fourth embodiment of a skin stretching device 301 exhibiting a plurality of curved shaft members 302, 304. According to the preferred configuration, the device includes a relatively longer curved shaft 302 having teeth 343 on an upper surface thereof. A distal end of the longer shaft 302 exhibits a retaining member 347, which exhibits a skin insertion needle 306 for insertion into the skin along a wound margin. The preferred configuration also includes a shorter curved shaft 304 exhibiting a retaining member 349, which exhibits a skin insertion needle 308 attached to a distal end thereof. The shorter shaft 304 is slidably disposed in a groove 345 provided in a lower surface of the longer shaft 302 and is anchored to the contracting mechanism 314 which is shaped to accommodate the curved shafts.

According to a preferred method, a skin closing apparatus is placed about the wound such that the skin insertion elements are disposed about opposing margins of the wound. Interdermal needles are then inserted into the skin along the edges of the wound. The skin insertion needles pierce the skin and engage with the interdermal needles. The edges of the wound are then approximated by applying force to a contracting mechanism (see FIGS. 1–6). When the edges of the wound are appropriately approximated, the edges of the wound can be sutured together.

It is also contemplated, for a wound of significant dimensions, to use the device to close an area of skin, apply sutures to that area and reposition the device on another part of that wound or on another wound on the same patient. It is further contemplated to use multiple devices on a single patient or wound simultaneously.

The illustrated embodiments are shown by way of example. The spirit and scope of the invention is not to be restricted by the preferred embodiments shown.

What is claimed is:

1. A skin stretching device for closing an open wound comprising:

a first elongated shaft exhibiting one or more skin engaging elements proximal to a first end thereof for engaging skin along a margin of the wound;

a second elongated shaft having a longitudinal axis parallel to a longitudinal axis of said first elongated shaft, said second shaft exhibiting one or more skin engaging elements proximal to a first end thereof for engaging skin along an opposing margin of the wound;

means for approximating said one or more skin engaging elements of said first elongated shaft toward said one or more skin engaging elements of said second elongated shaft; said means for approximating further comprising a contracting mechanism exhibiting a housing having an opening therein for receiving said second end of the first elongated shaft and said second end of the second elongated shaft; wherein the first ends of said first and second elongated shafts extend from the same side of the approximating means.

2. A skin stretching device according to claim 1, wherein said contracting mechanism includes a rack and ratchet mechanism disposed within said housing.

3. A skin stretching device according to claim 1, further comprising means for preventing backward movement of the first elongated shaft.

4. A skin stretching device accordingly to claim 1, wherein said housing for said contracting mechanism exhibits an elongated flange protruding from a surface thereof and surrounding longitudinal portions of said first elongated shaft and said second elongated shaft.

5. A skin stretching device according to claim 1, wherein a surface of the first elongated shaft slidably engages a surface of the second elongated shaft.

6. A skin stretching device according to claim 1, further comprising one or more interdermal needles for engagement by said skin insertion elements.

7. A skin stretching device according to claim 6, wherein said one or more interdermal needles comprises two interdermal needles.

8. A skin stretching device according to claim 1, wherein said first elongated shaft and said second elongated shaft each exhibit one skin insertion element.

9. A skin stretching device according to claim 1, wherein said first elongated shaft and said second elongated shaft each exhibit two or more skin insertion elements.

10. A skin stretching device according to claim 1 wherein said one or more skin insertion elements extend angularly downward from a distal end of said first elongated shaft and a distal end of said second elongated shaft.

11. A skin stretching device according to claim 1, wherein each said elongated shaft exhibits a square cross-section.

12. A skin stretching device according to claim 1, wherein each said elongated shaft exhibits a rectangular cross-section.

13. A skin stretching device according to claim 1, wherein each said elongated shaft exhibits a round cross-section.

14. A skin stretching device for closing an open wound comprising:

a first elongated shaft exhibiting one or more skin engaging elements for engaging skin along a margin of the wound, said one or more skin engaging elements extending from said first elongated shaft;

a second elongated shaft having a longitudinal axis parallel to a longitudinal axis of said first elongated shaft, said second shaft exhibiting one or more skin engaging elements for engaging skin along an opposing margin of the wound, said one or more skin engaging elements extending from said second elongated shaft;

a contracting mechanism for approximating said one or more skin engaging elements of said first elongated shaft toward said one or more skin engaging elements of said second elongated shaft; said contracting mechanism comprising;

a housing surrounding at least a longitudinal portion of the first elongated shaft and at least a longitudinal portion of the second elongated shaft;

a rack and ratchet mechanism disposed within said housing; said rack and ratchet mechanism comprising:

a slider block disposed within the housing of said contracting mechanism;

a guide pin attached to said slider block and slidably disposed within a longitudinal bore of said contracting mechanism housing;

a pawl pivotally connected to a lower portion of said slider block for exerting a driving force on the first elongated shaft;

a spring connected to said slider block for exerting a longitudinal force on said slider block.

15. A skin stretching device according to claim 14, further comprising a first lever, integral to an external surface of the housing of the contracting mechanism, and at least a second actuating lever pivot mounted to said slider block for actuating said pawl of the rack and ratchet mechanism.

16. A skin stretching device according to claim 14, further comprising a spacer block disposed between said slider block and said spring.

17. A skin stretching device for closing an open wound comprising:

a first elongated shaft exhibiting one or more skin engaging elements for engaging skin along a margin of the wound, said one or more skin engaging elements extending from said first elongated shaft;

a second elongated shaft having a longitudinal axis parallel to a longitudinal axis of said first elongated shaft, said second shaft exhibiting one or more skin engaging elements for engaging skin along an opposing margin of the wound, said one or more skin engaging elements extending from said second elongated shaft;

a contracting mechanism for approximating said one or more skin engaging elements of said first elongated shaft toward said one or more skin engaging elements of said second elongated shaft; said contracting mechanism exhibiting a housing surrounding at least a longitudinal portion of the first elongated shaft and at least a longitudinal portion of the second elongated shaft;

means for preventing backward movement of the first elongated shaft; said means for preventing backward movement comprising:

a wedge located in a recess of said contracting mechanism housing, a surface of said wedge engaging a surface of the first elongated shaft;

a spring having a first end connected to a post protruding from an inner wall of said contracting mechanism housing, and a second end connected to said wedge.

18. A skin stretching device according to claim 17, wherein at least a portion of the surface of the wedge exhibits a knurled surface.

19. A skin stretching device according to claim 17, wherein at least a portion of the surface of the wedge exhibits a toothed surface.

20. A skin stretching device according to claim 17, wherein at least a portion of the surface of the wedge exhibits a smooth surface.

21. A skin stretching device according to claim 17, wherein said surface of said first elongated shaft exhibits a knurled surface.

22. A skin stretching device according to claim 17, wherein said surface of said first elongated shaft exhibits a toothed surface.

23. A skin stretching device according to claim 17, wherein said surface of said first elongated shaft exhibits a smooth surface.

24. A skin stretching device for closing an open wound comprising:

a first elongated shaft exhibiting one or more skin engaging elements for engaging skin along a margin of the wound, said one or more skin engaging elements extending from said first elongated shaft;

a second elongated shaft having a longitudinal axis parallel to a longitudinal axis of said first elongated shaft, said second shaft exhibiting one or more skin engaging elements for engaging skin along an opposing margin of the wound, said one or more skin engaging elements extending from said second elongated shaft;

a contracting mechanism for approximating said one or more skin engaging elements of said first elongated shaft toward said one or more skin engaging elements of said second elongated shaft; said contracting mechanism exhibiting a housing surrounding at least a longitudinal portion of the first elongated shaft and at least a longitudinal portion of the second elongated shaft, wherein a first end of the first elongated shaft protrudes from an aperture in said housing' and a first end of the second elongated shaft abuts a surface located within said housing.

25. A skin stretching device according to claim 24, wherein the first elongated shaft exhibits a length greater than a length of the second elongated shaft.

26. A skin stretching device according to claim 24, wherein a surface of the first elongated shaft slidably engages a surface of the second elongated shaft.

27. A skin stretching device for closing an open wound comprising:

a first elongated shaft exhibiting one or more skin engaging elements for engaging skin along a margin of the wound, said one or more skin engaging elements extending from said first elongated shaft;

a second elongated shaft having a longitudinal axis parallel to a longitudinal axis of said first elongated shaft, said second shaft exhibiting one or more skin engaging elements for engaging skin along an opposing margin of the wound, said one or more skin engaging elements extending from said second elongated shaft;

means mechanism for approximating said one or more skin engaging elements of said first elongated shaft toward said one or more skin engaging elements of said second elongated shaft; said first elongated shaft and the second elongated shaft each exhibiting a rotating platform which exhibits a plurality of skin insertion elements.

28. A skin stretching device for closing an open wound comprising:

a first elongated shaft exhibiting one or more skin engaging elements for engaging skin along a margin of the wound, said one or more skin engaging elements extending from said first elongated shaft;

a second elongated shaft having a longitudinal axis parallel to a longitudinal axis of said first elongated shaft, said second shaft exhibiting one or more skin engaging elements for engaging skin along an opposing margin of the wound, said one or more skin engaging elements extending from said second elongated shaft;

a contracting mechanism for approximating said one or more skin engaging elements of said first elongated shaft toward said one or more skin engaging elements of said second elongated shaft; said contracting mechanism exhibiting a housing surrounding at least a longitudinal portion of the first elongated shaft and at least a longitudinal portion of the second elongated shaft, wherein said housing for said contracting mechanism exhibits an external tension indicator.

29. A skin stretching device according to claim 28, wherein said external tension indicator comprises a plurality of grooves formed in external lateral sides of the housing of the contacting mechanism, and configured to indicate varying levels of tension exerted upon the margins of the wound by the contracting mechanism.

30. A skin stretching device according to claim 28, further comprising means for selectively controlling the amount of tension applied to the margins of the wound.

31. A skin stretching device according to claim 30, wherein said means for selectively controlling tension comprises a tension control knob attached to an end of a slide pin protruding from a longitudinal bore in said housing, said knob exhibiting a plurality of internal longitudinal grooves for selectively receiving a lug protruding from a surface of the protruding end of said slide pin.

32. A skin stretching device according to claim 30, wherein said tension control element further includes external visual indicia for indicating the amount of tension to be exerted upon the margins of the wound.

33. A skin stretching device for closing a skin defect comprising:
  a contracting mechanism exhibiting a housing having an opening therein;
  a first elongated shaft member exhibiting one or more skin engaging elements proximal to a first end thereof for engaging skin along a margin of the skin defect, a second end of said first elongated shaft member extending into said housing through a first end of said opening; and
  a second elongated shaft member having a surface in sliding contact with a surface of said first elongated shaft member, said second elongated shaft member exhibiting one or more skin engaging elements proximal to a first end thereof for engaging skin along an opposing margin of the skin defect, a second end of said second elongated shaft member extending into said housing through the first end of said opening.

34. A skin stretching device according to claim 33, further comprising one or more interdermal needles for engagement by said skin engaging element of said first elongated shaft member and said skin engaging element of said second elongated shaft member.

35. A skin stretching device according to claim 34, wherein said one or more interdermal needles comprises a first interdermal needle for insertion along said margin of the skin defect and a second interdermal needle for insertion along said opposing margin of the skin defect.

36. A skin stretching device according to claim 33, wherein said first elongated shaft member and said second elongated shaft member each exhibit a curved configuration.

37. A skin stretching device according to claim 33, wherein a surface of the first elongated shaft member exhibits a longitudinal slot for slidably receiving said second elongated member.

38. A method of stretching skin to close a wound comprising the steps of:
  inserting interdermal needles into skin along margins of the wound;
  positioning a plurality of skin stretching devices, each said skin stretching device comprising a first retracting mechanism exhibiting an elongated shaft member and a skin engaging element and a second retracting mechanism exhibiting an elongated shaft member and a skin engaging element, about the wound such that said skin engaging element of said first retracting mechanism and said skin engaging element of said second retracting mechanism are proximal to said interdermal needles; and
  exerting a force upon a contracting mechanism of each of said plurality of skin stretching devices so that the skin engaging element of said first retracting mechanism and the skin engaging element of said second retracting mechanism engage the interdermal needles and approximate opposing margins of the wound.

39. The method of stretching skin to close a wound according to claim 38, wherein said step of inserting interdermal needles comprises the steps of:
  inserting a first interdermal needle into skin along a first margin of the wound; and
  inserting a second interdermal needle into skin along a second, opposing margin of the wound.

40. The method of stretching skin to close a wound according to claim 38, wherein said step of positioning a plurality of skin stretching devices further comprises the step of:
  piercing the skin with skin engaging elements extending from said independent retracting mechanisms.

41. A method of stretching skin to close a wound comprising the steps of:
  inserting interdermal needles into skin along margins of the wound;
  positioning a skin stretching device having a first elongated shaft member exhibiting a skin engaging element extending from a surface thereof and a second elongated shaft member exhibiting a skin engaging element extending from a surface thereof, about the wound such that said skin engaging element of said first elongated shaft member is proximal to one of said interdermal needles and said skin engaging element of said second elongated shaft member is proximal to another of said interdermal needles; and
  exerting a force upon a contracting mechanism of said skin stretching device so that the skin engaging element of said first elongated member engages said one of said interdermal needles and the skin engaging element of said second elongated member engages said another of said interdermal needles interdermal needles and approximate opposing margins of the wound.

42. The method of stretching skin to close a wound according to claim 41, wherein said step of inserting interdermal needles comprises the steps of:
  inserting a first interdermal needle into skin along a first margin of the wound; and
  inserting a second interdermal needle into skin along a second, opposing margin of the wound.

43. The method of stretching skin to close a wound according to claim 41, wherein said step of positioning a skin stretching device comprises positioning a plurality of skin stretching devices about said wound.

* * * * *